United States Patent
Wang

(10) Patent No.: US 10,117,871 B2
(45) Date of Patent: Nov. 6, 2018

(54) 3-HYDROXYPYRIMIDINE-2,4-DIONE-5-CARBOXAMIDES AS POTENT INHIBITORS OF HIV

(71) Applicant: Regents of the University of Minnesota, Minneapolis, MN (US)

(72) Inventor: Zhengqiang Wang, Eden Prairie, MN (US)

(73) Assignee: Regents of the University of Minnesota, Minneapolis, MN (US)

(*) Notice: Subject to any disclaimer, the term of this patent is extended or adjusted under 35 U.S.C. 154(b) by 0 days.

(21) Appl. No.: 15/553,508

(22) PCT Filed: Mar. 3, 2016

(86) PCT No.: PCT/US2016/020751
§ 371 (c)(1),
(2) Date: Aug. 24, 2017

(87) PCT Pub. No.: WO2016/141220
PCT Pub. Date: Sep. 9, 2016

(65) Prior Publication Data
US 2018/0028535 A1 Feb. 1, 2018

Related U.S. Application Data

(60) Provisional application No. 62/127,373, filed on Mar. 3, 2015.

(51) Int. Cl.
A61K 31/513 (2006.01)
C07D 239/557 (2006.01)
A61K 31/03 (2006.01)

(52) U.S. Cl.
CPC ........ A61K 31/513 (2013.01); C07D 239/557 (2013.01); *A61K 31/03* (2013.01); *C12N 2740/16063* (2013.01)

(58) Field of Classification Search
CPC .. A61K 31/513; A61K 31/03; C07D 239/557; C12N 2740/16063
(Continued)

(56) References Cited

U.S. PATENT DOCUMENTS 5,283,248 A * 2/1994 Hubschwerlen ...... C07C 275/40
514/217.06
7,790,734 B2 9/2010 Cao

FOREIGN PATENT DOCUMENTS

EP 1541562 A1 6/2005
WO WO-9743266 A1 11/1997
(Continued)

OTHER PUBLICATIONS

"International Application Serial No. PCT/US2016/020751, International Preliminary Report on Patentability dated Sep. 14, 2017", 8 pgs.
(Continued)

Primary Examiner — Kristin A Vajda
(74) Attorney, Agent, or Firm — Schwegman Lundberg & Woessner, P.A.

(57) ABSTRACT

Various embodiments described herein are directed to compounds of formula (I), (II), (III) or (IV) for use as potent inhibitors of HIV integrase and for treatment of patients afflicted with AIDS. A major challenge of human immunodeficiency virus (HIV) chemotherapy continues to be the inevitable selection of resistance by the virus towards known drug regimens. Treating resistant HIV strains calls for novel antivirals with unique structural cores. Some embodiments are directed to compounds featuring a 3-hydroxypyrimidine-2,4-dione-5-carboxamide core that consistently confers low nanomolar potencies against HIV-1 in cell culture. Biochemical testing and molecular modeling results corroborate an antiviral mechanism of action of inhibiting integrase strand transfer (INST). Preliminary testing against raltegravir-resistant HIVs showed marginal cross resistance, suggesting that the chemotypes of the various embodiments described herein could fit an inhibitory profile of second generation INSTIs.

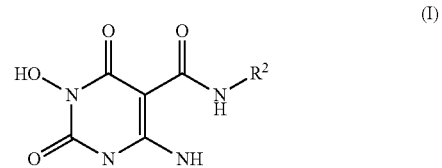

(I)

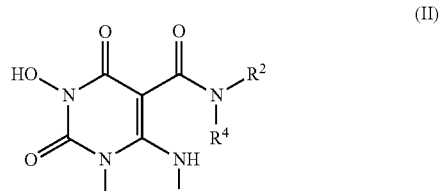

(II)

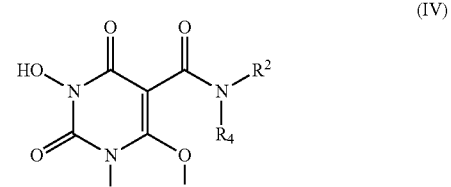

(IV)

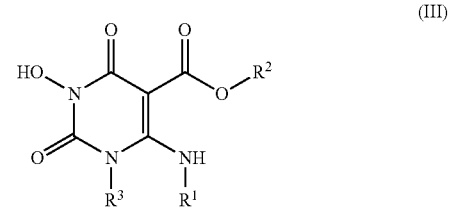

(III)

14 Claims, 3 Drawing Sheets

(58) Field of Classification Search
USPC .......................................................... 514/274
See application file for complete search history.

(56) References Cited

FOREIGN PATENT DOCUMENTS

| WO | WO-2012047993 | A2 | 4/2012 |
|----|---------------|----|--------|
| WO | WO-2012085003 | A1 | 6/2012 |
| WO | WO-2014160185 | A2 | 10/2014 |
| WO | WO-2016141220 | A1 | 9/2016 |

OTHER PUBLICATIONS

"International Application Serial No. PCT/US2016/020751, International Search Report dated May 10, 2016", 5 pgs.
"International Application Serial No. PCT/US2016/020751, Written Opinion dated May 10, 2016", 6 pgs.
"CAS Registry Number 1396785-58-2", Company: Life Chemicals, (2018), 3 pgs.
"Compound Summary, Catalogue number: AKOS011828445", AKos Consulting & Solutions GmbH (Germany), [online]. [retrieved on Jun. 1, 2018]. Retrieved from the Internet: <URL: https://pubchem.ncbi.nlm.nih.gov/compound/62538088>, (2018), 10 pgs.
Billamboz, Muriel, et al., "4-Substituted 2-Hydroxyisoquinoline-1,3(2H,4H)-diones as a Novel Class of HIV-1 Integrase Inhibitors", ACS Med. Chem. Lett, 4(7), (2013), 606-611.
Reddy, K. K., et al., "Identification of potential HIV-1 integrase strand transfer inhibitors: In silico virtual screening and QM/MM docking studies", (Abstract), SAR and QSAR in Environmental Research, 24:7, (2013), 581-595, (2013), 1 pg.
Tang, J., "3-Hydroxypyrimidine-2,4-diones as an Inhibitor Scaffold of HIV Integrase", HHS Public Access, published in final edited form as: J. Med. Chem., 54(7), (2011), 2282-2292, (2011), 31 pgs.
Tang, Jing, et ai., "6-Benzol-3-hydroxypyrimidine-2,4-diones as Dual Inhibitors of HIV Reverse Transcriptase and Integrase", Bioorganic & Medicinal Chemistry Letters, 21(8), (2011), 2400-2402.
Vernekar, Sanjeef Kumar V., et al., "Double-Winged 3-Hydroxypyrimidine-2,4-diones: Potent and Selective Inhibition against HIV-1 RNase H with Significant Antiviral Activity", J. Med. Chem., 2017, 60 (12), pp. 5045-5056, (May 19, 2017).
Wu, Bulan, et al., "3-Hydroxypyrimidine-2,4-dione-5-N-benzylcarboxamides Potently Inhibit HIV-1 Integrase and RNase H", J Med Chem. 2016 Jul. 14; 59(13); 6136-6148. (2016), 36 pgs.

* cited by examiner

Raltegravir

Evitegravir

Dolutegravir

3-HYDROXYPYRIMIDINE-2,4-DIONE-5-CARBOXAMIDES AS POTENT INHIBITORS OF HIV

CROSS-REFERENCE TO RELATED APPLICATIONS

This application is a U.S. national stage application filed under 35 U.S.C. § 371 from International Application Serial No. PCT/US2016/020751, which was filed Mar. 3, 2016, and published as WO2016/141220 on Sep. 9, 2016, which claims the benefit of U.S. Provisional Appl. Ser. No. 62/127,373, filed Mar. 3, 2015, the entire disclosure of which are incorporated by reference as if fully set forth herein.

STATEMENT OF GOVERNMENT RIGHTS

This invention was made with government support under AI100890 awarded by the National Institutes of Health. The government has certain rights in the invention.

BACKGROUND

Human Immunodeficiency Virus (HIV) and the human disease it causes, Acquired Immunodeficiency Syndrome (AIDS), remains a significant global healthcare challenge with an estimated 34 million people living with AIDS. Due to the lack of effective vaccine and the persistence of viral reservoir, management of HIV/AIDS relies heavily on chemotherapy. Unfortunately, only about one in every five infected individuals has the access to antivirals. Therefore, there is always a need and market for novel antivirals against HIV.

BRIEF DESCRIPTION OF THE FIGS

DETAILED DESCRIPTION

Figure 1:
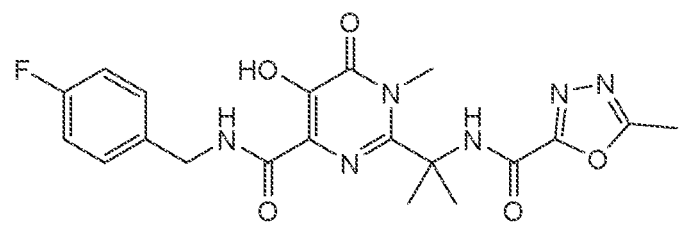
FIG. 1 shows the chemical structures of three known integrase inhibitors.
Figure 1:
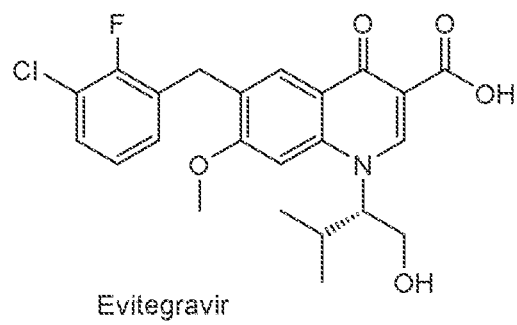
Figure 1:
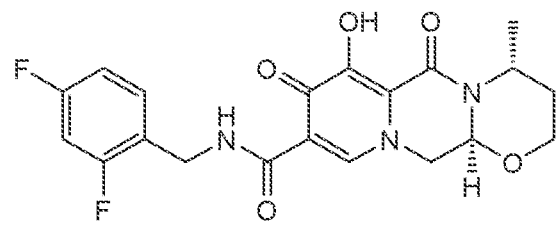

The compounds of the various embodiments described herein target HIV integrase, an enzyme essential for viral replication and a validated target for antiviral development. Although there are three integrase inhibitors approved by FDA, their antiviral efficacy will be compromised by HIV's ability to develop resistance. Existing bioactive compounds believed to act as integrase inhibitors, having some efficacy against HIV, include raltegravir, elvitegravir, and dolutegravir (see FIG. 1). Reference is made herein to PCT application PCT/US2011/054916, published as WO2012/047993, the disclosure of which is incorporated herein by reference in its entirety.

The expression "effective amount", when used to describe therapy to an individual suffering from AIDS, refers to the quantity or concentration of a compound of the invention that is effective to inhibit or otherwise act on HIV by means of inhibition of the HIV integrase enzyme, in the individual's tissues wherein HIV involved in the disorder, wherein such inhibition or other action occurs to an extent sufficient to produce a beneficial therapeutic effect.

All single enantiomer, diastereomeric, and racemic forms of a structure are intended, unless a particular stereochemistry or isomeric form is specifically indicated. In several instances though an individual stereoisomer is described among specifically claimed compounds, the stereochemical designation does not imply that alternate isomeric forms are less preferred, undesired, or not claimed. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

As used herein, the terms "stable compound" and "stable structure" are meant to indicate a compound that is sufficiently robust to survive isolation to a useful degree of purity from a reaction mixture, and formulation into an efficacious therapeutic agent. Only stable compounds are contemplated herein.

When a number of carbon atoms in a group, e.g., an alkyl, alkenyl, alkynyl, cycloalkyl, aryl, etc., is specified as a range, each individual integral number representing the number of carbon atoms is intended. For example, recitation of a ($C_1$-$C_6$)alkyl group indicates that the alkyl group can be any of methyl, ethyl, propyl, isopropyl, butyl, sec-butyl, isobutyl, tert-butyl, pentyl, sec-pentyl, isopentyl, neopentyl, hexyl, isohexyl, etc. It is understood that a specification of a number of carbon atoms must be an integer.

The term "alkyl," as used herein, refers to substituted or unsubstituted straight chain and branched alkyl groups and cycloalkyl groups having from 1 to 50 carbon atoms ($C_1$-$C_{50}$; e.g., $C_{10}$-$C_{30}$, $C_{12}$-$C_{18}$; $C_1$-$C_{20}$, $C_1$-$C_{10}$; $C_1$-$C_8$; $C_1$-$C_6$, and $C_1$-$C_3$). Examples of straight chain alkyl groups include those with from 1 to 8 carbon atoms ($C_1$-$C_8$) such as methyl, ethyl, n-propyl, n-butyl, n-pentyl, n-hexyl, n-heptyl, n-octyl groups. Examples of branched alkyl groups include, but are not limited to, isopropyl, iso-butyl, sec-butyl, t-butyl, neopentyl, isopentyl, 2,2-dimethylpropyl, and isostearyl groups. Examples of cycloalkyl groups include cyclopropyl, cyclobutyl, cyclopentyl, and cyclohexyl groups.

The term "aryl," as used herein, refers to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 18 carbons ($C_6$-$C_{18}$; e.g., $C_6$-$C_{12}$; $C_6$-$C_{10}$; and $C_{12}$-$C_{18}$) in the ring portions of the groups. Representative substituted aryl groups can be mono-substituted or substituted more than once, such as, but not limited to, 2-, 3-, 4-, 5-, or 6-substituted phenyl or 2-8 substituted naphthyl groups.

The alkyl, cycloalkyl, aryl, etc., groups described herein can be substituted or unsubstituted. The term "substituted" as used herein refers to a group (e.g., alkyl and aryl) or molecule in which one or more hydrogen atoms contained thereon are replaced by one or more "substituents." The term "substituent" as used herein refers to a group that can be or is substituted onto a molecule or onto a group. Examples of substituents include, but are not limited to, a halogen (e.g., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, or C(=NOR)R, wherein R can be, for example, hydrogen, alkyl, acyl, cycloalkyl, aryl, aralkyl, heterocyclyl, heteroaryl, or heteroarylalkyl.

The term "acyl" as used herein refers to a group containing a carbonyl moiety wherein the group is bonded via the carbonyl carbon atom. The carbonyl carbon atom is also bonded to another carbon atom, which can be part of a substituted or unsubstituted alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-40, 6-10, 1-5 or 2-5 additional carbon atoms bonded to the carbonyl group. An acryloyl group is an example of an acyl group. An acyl group can also include heteroatoms within the meaning here. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "aralkyl," "arylalkyl," and "aryl-alkyl" as used herein refers to alkyl groups as defined herein in which a hydrogen or carbon bond of an alkyl group is replaced with a bond to an aryl group as defined herein. Representative aralkyl groups include benzyl and phenylethyl groups.

The term "heteroaralkyl" and "heteroarylalkyl" as used herein refers to alkyl groups as defined herein in which a hydrogen or carbon bond of an alkyl group is replaced with a bond to a heteroaryl group as defined herein.

The term "heterocyclyl" as used herein refers to substituted or unsubstituted aromatic and non-aromatic ring compounds containing 3 or more ring members, of which, one or more is a heteroatom such as, but not limited to, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. In some embodiments, heterocyclyl groups include heterocyclyl groups that include 3 to 8 carbon atoms (C$_3$-C$_8$), 3 to 6 carbon atoms (C$_3$-C$_6$) or 6 to 8 carbon atoms (C$_6$-C$_8$). A heterocyclyl group designated as a C$_2$-heterocyclyl can be a 5-ring with two carbon atoms and three heteroatoms, a 6-ring with two carbon atoms and four heteroatoms and so forth. Likewise a C$_4$-heterocyclyl can be a 5-ring with one heteroatom, a 6-ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. Representative heterocyclyl groups include, but are not limited to piperidynyl, piperazinyl, morpholinyl, furanyl, pyrrolidinyl, pyridinyl, pyrazinyl, pyrimidinyl, triazinyl, thiophenyl, tetrahydrofuranyl, pyrrolyl, oxazolyl, imidazolyl, triazyolyl, tetrazolyl, benzoxazolinyl, and benzimidazolinyl groups.

Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention. "Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

A "hydrate" is a compound that exists in a composition with water molecules. The composition can include water in stoichiometric quantities, such as a monohydrate or a dihydrate, or can include water in random amounts. As the term is used herein a "hydrate" refers to a solid form, i.e., a compound in water solution, while it may be hydrated, is not a hydrate as the term is used herein. Compounds of the invention or compounds used for practicing a method of the invention can be in the form of a hydrate.

A "solvate" is a similar composition except that a solvent other that water replaces the water. For example, methanol or ethanol can form an "alcoholate," which can again be stoichiometric or non-stoichiometric. As the term is used herein a "solvate" refers to a solid form, i.e., a compound in solution in a solvent, while it may be solvated, is not a solvate as the term is used herein. Compounds of the invention or compounds used for practicing a method of the invention can be in the form of a solvate, e.g., of an alcohol or the like.

HIV/AIDS remains a significant global healthcare challenge with an estimated 34 million people living with AIDS. Due to the lack of effective vaccine and the persistence of viral reservoir, management of HIV/AIDS relies heavily on chemotherapy. Currently there are numerous FDA-approved drugs of five different classes in HIV antiviral repertoire: nucleoside reverse transcriptase inhibitors (NRTIs) that typically form the backbone of all treatment regimens; non-nucleoside reverse transcriptase inhibitors (NNRTIs); protease inhibitors (PIs); Integrase Strand Transfer Inhibitor (INSTIs); and entry inhibitors. As successful as HIV chemotherapies have been in transforming HIV/AIDS into a clinically manageable disease, they can also be easily plagued by the inevitable selection of resistant viral strains. Therefore, sustained success in HIV chemotherapy requires novel antivirals with structurally unique pharmacophore cores. Previously-developed chemotypes featuring a 3-hydroxypyrimidine-2,4-dione core[1-3] have shown broad antiviral activities against HIV-1, hepatitis C virus (HCV), and hepatitis B virus (HBV) by targeting RT and IN (HIV), RNase H (HIV and HBV), NS5B polymerase (HCV).

Some embodiments described herein that have a 3-hydroxypyrimidine-2,4-dione scaffold with a unique C5 carboxamide moiety demonstrate extraordinary antiviral potencies against HIV-1, and that the antiviral activity could be linked to potent and specific inhibition of INST.

Various embodiments described herein relate to a new class of compounds, 3-hydroxypyrimidine-2,4-dione-5-carboxamides, for use as potent inhibitors of HIV and for treatment of patients afflicted with AIDS.

Various embodiments described herein relate to 3-hydroxypyrimidine-2,4-dione-5-carboxamide compounds of formula (I)

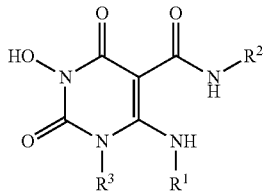
(I)

wherein $R^1$ is H, $(C_1-C_6)$alkyl, $(C_3-C_6)$ cycloalkyl, or $(C_6-C_{12})$aryl; $R^2$ is benzyl, which can be unsubstituted or can be substituted with one to three occurrences of a substituent independently selected from the group consisting of fluoro, chloro, bromo, iodo, cyano, nitro, $(C_1-C_6)$alkyl, $(C_1-C_6)$alkoxy, $(C_1-C_6)$alkoxycarbonyl, $(C_1-C_6)$alkylC(=O)NH, $(C_1-C_6)$alkylNHC(=O), $((C_1-C_6)$alkyl$)_2$NC(=O), $(C_1-C_6)$alkylSO$_2$, $(C_1-C_6)$alkylNHSO$_2$, and $((C_1-C_6)$alkyl$)_2$NSO$_2$; $R^3$ is H, $(C_1-C_6)$alkyl, $(C_3-C_6)$ cycloalkyl, or $(C_6-C_{12})$aryl; or a pharmaceutically acceptable salt thereof.

For example, the invention can provide a 3-hydroxypyrimidine-2,4-dione-5-carboxamide compound of formula (IA)

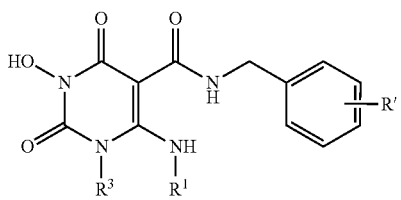
(IA)

wherein $R^1$ is H, $(C_1-C_6)$alkyl or $(C_3-C_6)$ cycloalkyl, and R' is zero to three occurrences of a substituent independently selected from the group consisting of fluoro, chloro, bromo, iodo, cyano, nitro, $(C_1-C_6)$alkyl, $(C_1-C_6)$alkoxy, $(C_1-C_6)$alkoxycarbonyl, $(C_1-C_6)$alkylC(=O)NH, $(C_1-C_6)$alkylNHC(=O), $((C_1-C_6)$alkyl$)_2$NC(=O), $(C_1-C_6)$alkylSO$_2$, $(C_1-C_6)$alkylNHSO$_2$, and $((C_1-C_6)$alkyl$)_2$NSO$_2$; $R^2$ is benzyl, which can be unsubstituted or can be substituted with one to three occurrences of a substituent independently selected from the group consisting of fluoro, chloro, bromo, iodo, cyano, nitro, $(C_1-C_6)$alkyl, $(C_1-C_6)$alkoxy, $(C_1-C_6)$alkoxycarbonyl, $(C_1-C_6)$alkylC(=O)NH, $(C_1-C_6)$alkylNHC(=O), $((C_1-C_6)$alkyl$)_2$NC(=O), $(C_1-C_6)$alkylSO$_2$, $(C_1-C_6)$alkylNHSO$_2$, and $((C_1-C_6)$alkyl$)_2$NSO$_2$; $R^3$ is H, $(C_1-C_6)$alkyl, $(C_3-C_6)$ cycloalkyl, or $(C_6-C_{12})$aryl; or a pharmaceutically acceptable salt thereof.

For instance, $R^1$ can be H, methyl or ethyl; for instance, $R^3$ can be H.

Various embodiments described herein relate to 3-hydroxypyrimidine-2,4-dione-5-carboxamide compounds of formula (II)

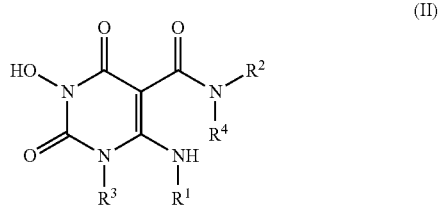
(II)

wherein $R^1$ is H, $(C_1-C_6)$alkyl, $(C_3-C_6)$ cycloalkyl, or $(C_6-C_{12})$aryl; $R^2$ is hydrogen, benzyl, which can be unsubstituted or can be substituted with one to three occurrences of a substituent independently selected from the group consisting of fluoro, chloro, bromo, iodo, cyano, nitro, $(C_1-C_6)$alkyl, $(C_1-C_6)$alkoxy, $(C_1-C_6)$alkoxycarbonyl, $(C_1-C_6)$alkylC(=O)NH, $(C_1-C_6)$alkylNHC(=O), $((C_1-C_6)$alkyl$)_2$NC(=O), $(C_1-C_6)$alkylSO$_2$, $(C_1-C_6)$alkylNHSO$_2$, and $((C_1-C_6)$alkyl$)_2$NSO$_2$; $R^3$ is H, $(C_1-C_6)$alkyl, $(C_3-C_6)$ cycloalkyl, or $(C_6-C_{12})$aryl or $R^1$ and $R^3$ can form a five- or six-membered heterocyclic ring; and $R^4$ is a hydrogen or $(C_1-C_6)$alkyl; or a pharmaceutically acceptable salt thereof. In some embodiments, $R^1$ and $R^3$ can form a five- or six-membered heterocyclic ring.

Various embodiments described herein relate to 3-hydroxypyrimidine-2,4-dione-5-carboxylate compounds of formula (III)

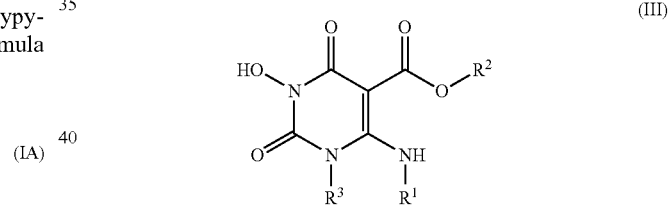
(III)

wherein $R^1$ is H, $(C_1-C_6)$alkyl, $(C_3-C_6)$ cycloalkyl, or $(C_6-C_{12})$aryl; $R^2$ is $(C_3-C_6)$ cycloalkyl, or $(C_6-C_{12})$aryl; and $R^3$ is H, $(C_1-C_6)$alkyl, $(C_3-C_6)$ cycloalkyl, or $(C_6-C_{12})$aryl or $R^1$ and $R^3$ can form a five- or six-membered heterocyclic ring; or a pharmaceutically acceptable salt thereof. In some embodiments. $R^1$ and $R^3$ can form a five- or six-membered heterocyclic ring.

Various embodiments described herein relate to 3-hydroxypyrimidine-2,4-dione-5-carboxylate compounds of formula (IV)

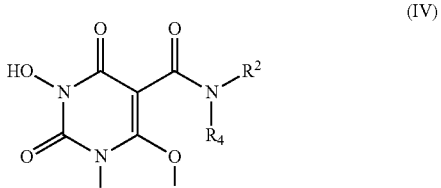
(IV)

wherein $R^1$ is H, $(C_1-C_6)$alkyl, $(C_3-C_6)$ cycloalkyl, or $(C_6-C_{12})$aryl; $R^2$ is $(C_3-C_6)$ cycloalkyl, or $(C_6-C_{12})$aryl; $R^3$ is H, ($C_1$-$C_6$)alkyl, ($C_3$-$C_6$) cycloalkyl, or ($C_6$-$C_{12}$)aryl or $R^1$ and $R^3$ can form a five- or six-membered heterocyclic ring; and $R^4$ is a hydrogen or ($C_1$-$C_6$)alkyl; or a pharmaceutically acceptable salt thereof.

The invention further provides pharmaceutical composition comprising a compound of the invention and a pharmaceutically acceptable excipient.

In various embodiments, the invention can provide a method of inhibiting HIV integrase, comprising contacting the HIV integrase with an effective amount or concentration of a compound of formula (I) or a pharmaceutically acceptable salt thereof. The HIV integrase can be in an intact virus, for instance, within a human cell of a patient.

In various embodiments, the invention can provide a method of treatment of AIDS in a patient, comprising administering to the patient an effective dose of a compound of formula (I) or a pharmaceutically acceptable salt thereof.

Compounds of the present invention can be prepared by a person of ordinary skill in the art of organic synthesis using the procedures provided below in the Examples in conjunction with ordinary skill and knowledge.

Compounds of formula (I) (e.g., target compounds 7) were prepared via a concise and diverse synthetic route shown in Scheme 1. The synthesis started from commercially available hydroxyurea 1 which was O-benzylated with BnBr in the presence of KOH at reflux condition to provide 1-(benzyloxy)urea 2 in high yield.[4] Cyclocondensation of 1-(benzyloxy)urea 2 and diethyl malonate provided six-membered herterocycle compound 3-(benzyloxy)-6-hydroxypyrimidine-2,4(1H,3H)-dione 3 in moderate yield under microwave irradiation condition (150° C., 20 min) or under conventional heating (reflux, overnight).[5] Compound 3 was converted to key intermediate 3-(benzyloxy)-6-chloropyrimidine-2,4(1H,3H)-dione 4 in 88% yield by reacting with $POCl_3$ in the presence of $BnEt_3NCl$.[6] Reaction of intermediate chloride 4 with amine in the presence of N,N-dimethylaniline under microwave condition provided 6-amination product 5 in moderate to good yield.[7] The key carboxamide 6 was achieved via reacting 6-amino intermediate 5 with isocyanates or acylazide under microwave irradiation condition using nitrobenzene as solvent for a short time (210° C., 20-40 min, 60-100%) (Scheme 1),[8] a highly efficient method for small scale reaction. The final debenzylation of compounds 6 was achieved by treating with TFA under microwave condition[9] or via catalytic hydrogenation.

Scheme 1[a] Synthesis of chemotype 7 (formula (I))

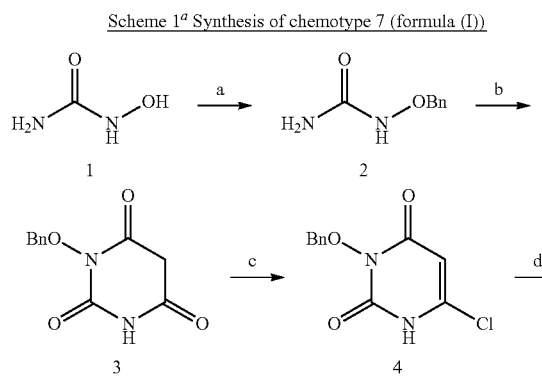

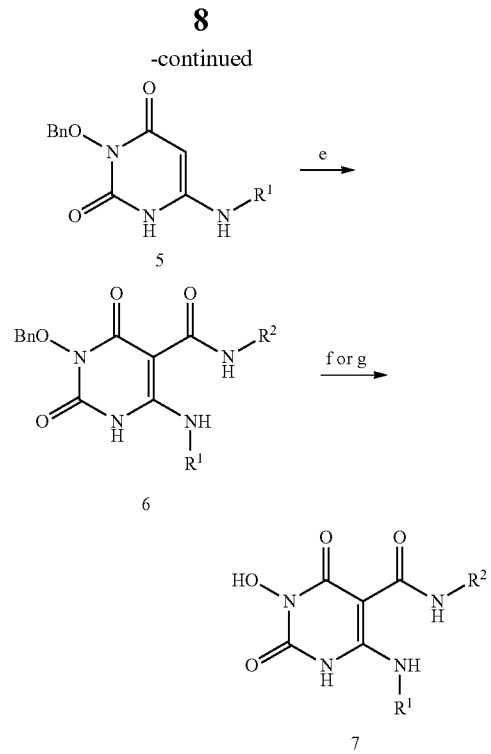

[a]Reagents and conditions: a) KOH, BnBr, MeOH, reflux, 6 h, 91%; b) $CH_2(COOEt)_2$, NaOEt, MW, 150° C., 20 min, 58%; c) $POCl_3$, $BnEt_3NCl$, 50° C., 6 h, 88%; d) $R^1$—$NH_2$, N,N-dimethylaniline, MW, 170° C., 20-25 min, 54%-78%; e) $R^2NCO$ (or $R^2CON_3$), $PhNO_2$, MW, 210° C., 20-40 min, 60-100%; f) Pd/C, $H_2$ 40~50 Psi, MeOH, 4-6 h, 82-97%; g) TFA, MW, 120° C., 35-55 min, 50-77%.

Alternatively, preparation of the carboxamide intermediate 6 can be achieved via a two-step reaction sequence (scheme 2). In this case, the amino intermediate 5 was treated with phenyl chloroformate and a base, such as pyridine, to give intermediate phenyl ester 8 which was converted amide 6 upon reacting with a primary amine under conventional heating or microwave conditions. Debenzylation with the same protocol afforded the desired chemotype 7.

For compounds of chemotype 7, compound bearing a non-hydrogen substituent on the pyrimidine nitrogen atom not bearing the hydroxyl group (i.e., a compound of formula (I) or of formula (IA) wherein $R^3$ is ($C_1$-$C_6$)alkyl, or ($C_6$-$C_{12}$)aryl), the sequence can be carried out in the same manner, except replacing intermediate 2 with an analogous intermediate bearing an alkyl or an aryl group on the carboxamido nitrogen atom that does not bear the O-Bn group. This can provide intermediate 5 bearing the alkyl or aryl substituent on the corresponding pyrimidine nitrogen atom. i.e., group $R^3$ of formula (I) or of formula (IA).

Scheme 2[a] Alternative synthesis of chemotype 7 (formula (I))

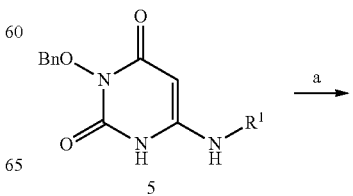

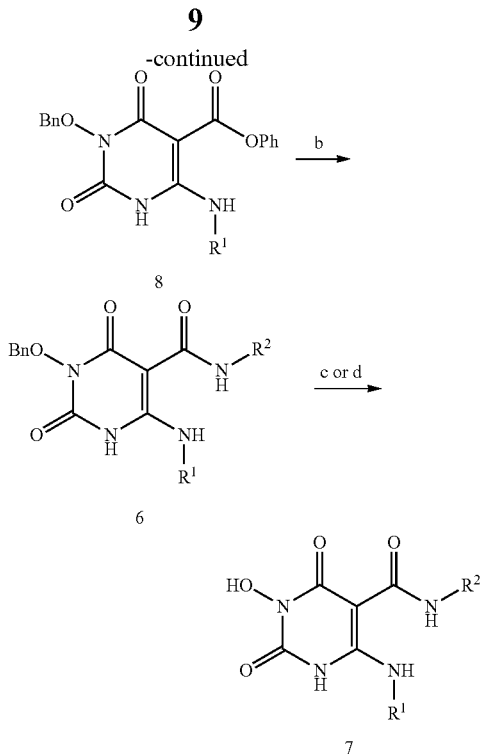

*Reagents and conditions: a) ClCO₂Ph, pyridine, rt, 2 h, 62%; b) R² — NH2, MW, dioxane, 100° C., 50 min, 82-92%; c) Pd/C, H₂, 40~50 Psi, MeOH, 4-6 h, 82-97%; d) TFA, MW, 120° C., 35-55 min, 50-77%.

Antiviral Testing.

The antiviral activity of newly synthesized analogues of chemotype 7 was evaluated against HIV-1IIIB in CEM-SS cells using an assay based on viral cytopathic effect (CPE). In this assay, the reduction of CPE was used to indicate the antiviral activity of a compound. All selected compounds were first screened under a single concentration (10 μM) and the results are summarized in Table 1. The most striking structure-activity-relationship (SAR) was that analogues with an aromatic amine at the C5 position ($R^1$=aryl, 7-i-7-iv, Table 1) were completely inactive and severely cytotoxic, whereas a small aliphatic amine substitution at the same position ($R^1$=alkyl, 7-v-7-xxiv, Table 1) conferred excellent antiviral activity without cytotoxicity, with the lone exception being the isopropylamino analogue (7-viii) which was inactive and cytotoxic. In addition, among all small alkyl groups for $R^1$, the ethyl group appeared to be optimal for antiviral potency. As far as the $R^2$ group is concerned, a mono- or disubstituted benzyl group appeared to benefit antiviral potency the most. Replacing the phenyl ring with an alkyl group in the carboxamide moiety (7-xxvii, $R^2$=CH₂CH₂Cl, Table 1) completely abrogated antiviral activity. Interestingly, antiviral activity was largely retained when an extra methylene group was added between the benzyl group and the carboxamide functionality (7-xxvi, Table 1), while deleting the methylene group of the benzyl group (7-xxv, Table 1) caused a complete loss of activity, suggesting that target binding by this terminal aromatic group requires structural flexibility.

TABLE 1

Anti-HIV-1 activity (CPE reduction %) of chemotype 7 (formula (I)) analogues at 10 μM

| Compound (7-) | $R^1$ | $R^2$ | CPE reduction % | Cell viability % |
|---|---|---|---|---|
| i | phenyl | benzyl | 0 | 21 |
| ii | 4-biphenyl | benzyl | 0 | 13 |
| iii | 4-biphenyl | 3-fluorobenzyl | 0 | 8.7 |

TABLE 1-continued
Anti-HIV-1 activity (CPE reduction %) of chemotype 7 (formula (I)) analogues at 10 μM
7
| Compound (7-) | R¹ | R² | CPE reduction % | Cell viability % |
|---|---|---|---|---|
| iv | 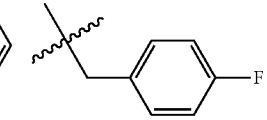 | 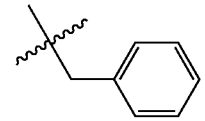 | 0 | 9.1 |
| v | CH₃ | 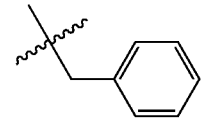 | 100 | 98 |
| vi | CH₂CH₃ | 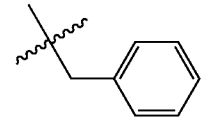 | 100 | 100 |
| vii | CH₂CH₂CH₃ |  | 100 | 97 |
| viii | 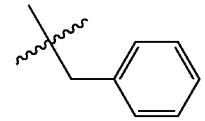 [SMILES: *Cc1ccccc1] | 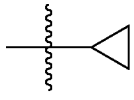 [SMILES: *C1CC1] | 0 | 17 |
| ix | 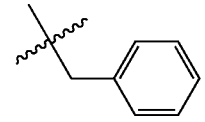 | 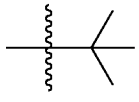 [SMILES: *C(C)(C)C] | 98 | 90 |
| x | 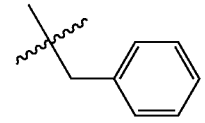 | 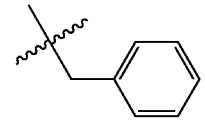 [SMILES: *Cc1ccccc1] | 98 | 91 |
| xi | H | 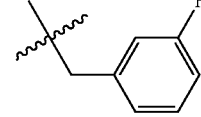 | 99 | 100 |
| xii | CH₃ |  | 100 | 95 |

TABLE 1-continued
Anti-HIV-1 activity (CPE reduction %) of chemotype 7 (formula (I)) analogues at 10 μM
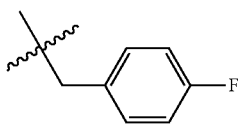 [SMILES: *Cc1ccc(F)cc1]
7
| Compound (7-) | R¹ | R² | CPE reduction % | Cell viability % |
|---|---|---|---|---|
| xiii | $CH_3$ | 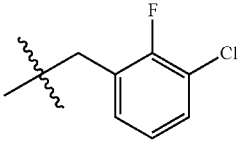 [SMILES: *Cc1cccc(Cl)c1F] | 100 | 89 |
| xiv | $CH_3$ | 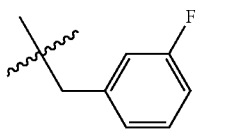 [SMILES: *Cc1cccc(F)c1] | 100 | 100 |
| xv | $CH_2CH_3$ | 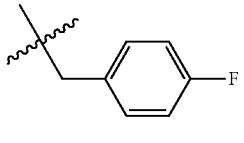 [SMILES: *Cc1ccc(F)cc1] | 100 | 90 |
| xvi | $CH_2CH_3$ | 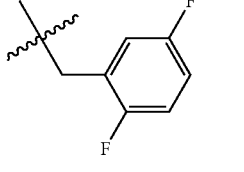 | 100 | 99 |
| xvii | $CH_2CH_3$ | 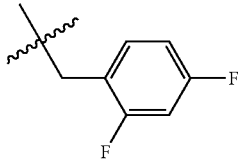 | 100 | 92 |
| xviii | $CH_2CH_3$ | 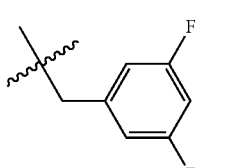 | 92 | 87 |
| xix | $CH_2CH_3$ | 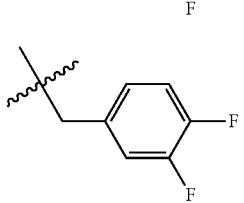 | 100 | 100 |
| xx | $CH_2CH_3$ |  | 100 | 100 |

TABLE 1-continued
Anti-HIV-1 activity (CPE reduction %) of chemotype 7 (formula (I)) analogues at 10 μM
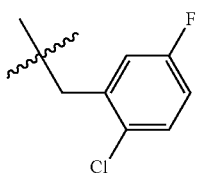 [SMILES: *Cc1cc(F)ccc1F]
7
| Compound (7-) | R¹ | R² | CPE reduction % | Cell viability % |
|---|---|---|---|---|
| xxi | CH₂CH₃ | 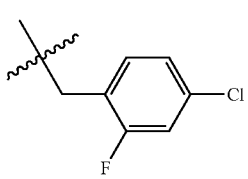 [SMILES: *Cc1ccc(Cl)cc1F] | 62 | 73 |
| xxii | CH₂CH₃ | 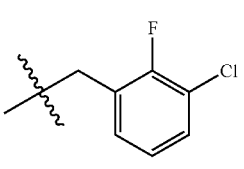 [SMILES: *Cc1cccc(Cl)c1F] | 100 | 100 |
| xxiii | CH₂CH₃ | 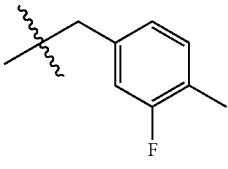 [SMILES: *Cc1ccc(C)c(F)c1] | 100 | 100 |
| xxiv | CH₂CH₃ | 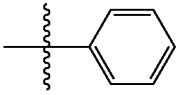 | 100 | 100 |
| xxv | CH₂CH₃ | 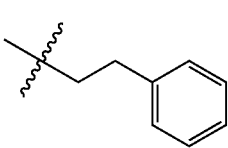 [SMILES: *CCc1ccccc1] | 11 | 27 |
| xxvi | CH₂CH₃ | 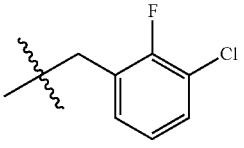 [SMILES: *Cc1cccc(Cl)c1F] | 99 | 87 |
| xxvii | CH₂CH₃ | CH₂CH₂Cl | 5.1 | 100 |
| xxviii | CH₂CH₂CH₃ |  | 33 | 48 |

TABLE 1-continued

Anti-HIV-1 activity (CPE reduction %) of chemotype 7 (formula (I)) analogues at 10 μM

| Compound (7-) | R¹ | R² | CPE reduction % | Cell viability % |
|---|---|---|---|---|
| xxix | 4-biphenyl | 2-fluorobenzyl | Not determined | Not determined |
| xxx | 4-biphenyl | 2,4-difluorobenzyl | Not determined | Not determined |
| xxxi | 4-biphenyl | 2,5-difluorobenzyl | Not determined | Not determined |
| xxxii | 4-biphenyl | 3,5-difluorobenzyl | Not determined | Not determined |
| xxxiii | 4-biphenyl | 2-fluoro-3-chlorobenzyl | Not determined | Not determined |
| xxxiv | $CH_2CH_3$ | H | Not determined | Not determined |
| xxxv | $CH_2CH_3$ | 4-fluorobenzyl | Not determined | Not determined |

Compounds 7-xxix-7-xxxv have an INST $IC_{50}$ of greater than about 100 μM.

To better gauge the antiviral potency, selected inhibitors with excellent CPE reduction and cell viability from this screening assay were further tested in a dose response fashion, from which the $EC_{50}$ and $CC_{50}$ were determined (Table 2). Remarkably all compounds tested showed nanomolar activity and five of the eight analogues were active in low nanomolar range ($EC_{50}$=15-61 nM), clearly demonstrating an antiviral potency comparable to that of FDA-approved AZT (NRTI) and raltegravir (RAL, INSTI). Although these analogues showed mild cytotoxicity in the range of 18-58 μM, the selectivity window (Table 2), particularly that for analogues 7-xvii (TI=1500) and 7-xxiii (TI=1200), is sufficiently large to warrant their further development.

TABLE 2

Dose-response anti-HIV testing of selected analogues

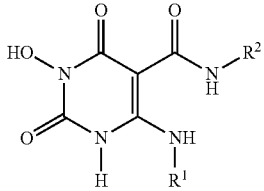

7

| Compound | EC$_{50}$ (μM)$^a$ | CC$_{50}$ (μM)$^b$ | TI$^c$ |
|---|---|---|---|
| 7-v | 0.83 | 58 | 70 |
| 7-vi | 0.061 | 23 | 380 |
| 7-xvi | 0.033 | 19 | 580 |
| 7-xvii | 0.032 | 47 | 1500 |
| 7-xx | 0.049 | 21 | 430 |
| 7-xxii | 0.19 | 19 | 100 |
| 7-xxiii | 0.015 | 18 | 1200 |
| 7-xxiv | 0.15 | 20 | 130 |
| AZT$^d$ | 0.080 | >10 | >130 |
| RAL$^d$ | 0.023 | >10 | >430 |

$^a$Concentration inhibiting virus replication by 50%.
$^b$Concentration resulting in 50% cell death.
$^c$Therapeutic index, defined by CC$_{50}$/EC$_{50}$.
$^d$EC$_{50}$ value determined from a different run of the same assay.

Antiviral Mechanism of Action

The structures shown below depict FDA-approved INSTIs (9-11) and one compound of the various embodiments described herein, namely, inhibitor 7-xvi. Each approved drug features a chelating triad (red) and a terminal benzyl group (blue) that constitute the pharmacophore of HIV-1 INSTIs. 7-xvi fits the pharmacophore with the same two structural features.

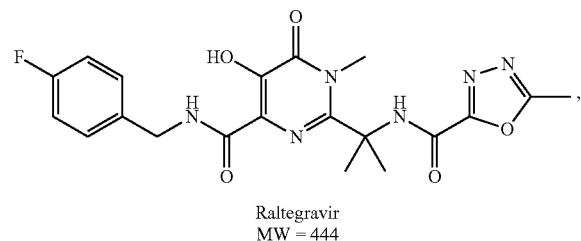

Raltegravir
MW = 444

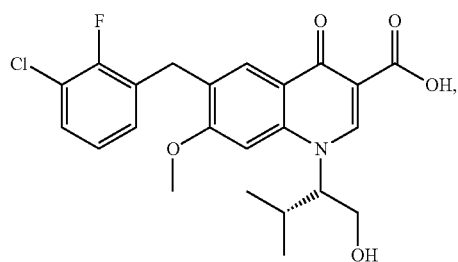

Elvitegravir
MW = 448

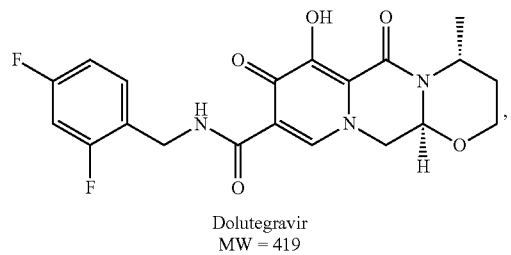

Dolutegravir
MW = 419

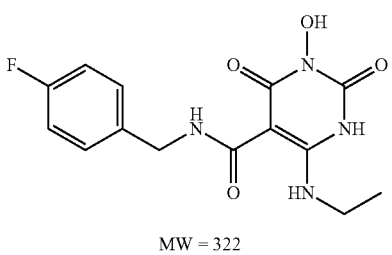

MW = 322

Chemotype 7 was rationally designed to selectively inhibit HIV-1 INST which is critical to HIV infection and the establishment of proviral latency[10-12] and represent a particular attractive target due to the lack of host cellular counterpart. In addition, IN uses the same active site (DD35E motif) for both the 3' processing and the ST steps and its inhibitors could benefit from a potentially high genetic barrier to resistance development. Selective ST inhibitors (STIs) all feature a diketoacid (DKA) functionality or its heterocyclic bioisosteres[13-17] along with a hydrophobic terminal benzyl moiety,[18-23] as demonstrated by all three FDA-approved INSTIs (FIG. 1): raltegravir (RAL, 9)[24, 25], elvitegravir (EVG, 10),[26] and dolutegravir (DTG, 11)[27, 28] which is a second-generation INSTI.[29] Significantly, chemotype 7 has the two structural determinants essential for INST binding and inhibition (FIG. 1). The overall shape and functionalities of 7 are particularly reminiscent to DTG, suggesting that the compounds of the various embodiments described herein can be second generation INSTIs. It is also noteworthy that the compounds of the various embodiments described herein a significant smaller "size" (MW for 7xvi=322; the MW for drugs 9-11 is in the range of 419-448) while supporting antiviral activities comparable to RAL and AZT (Table 2). This will allow significant room for optimization during further development. Nevertheless, all analogues for chemotype 7 were tested in a ST assay and the results are summarized in Table 3.

TABLE 3
Biochemical inhibition of 7 in the HIV-1 integrase strand transfer assay
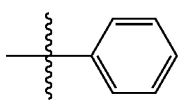
| Compound (7-) | $R^1$ | $R^2$ | INST $IC_{50}$ (µM) |
| --- | --- | --- | --- |
| i | 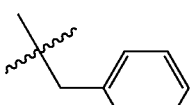 | 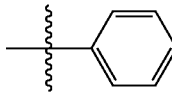 | >100 |
| ii | 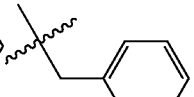 | 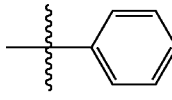 | >100 |
| iii | 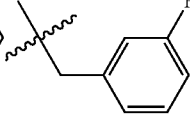 | 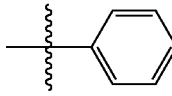 | >100 |
| iv | 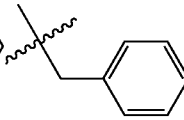 | 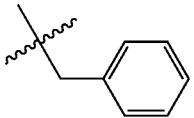 [SMILES: *Cc1ccccc1] | >100 |
| v | $CH_3$ | 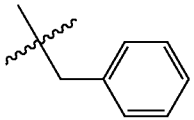 | 0.080 ± 0.007 |
| vi | $CH_2CH_3$ | 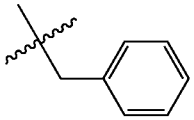 | 0.033 ± 0.004 |
| vii | $CH_2CH_2CH_3$ | 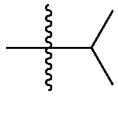 | 0.066 ± 0.016 |
| viii | 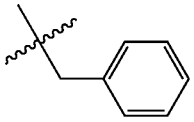 [SMILES: *Cc1ccccc1] | 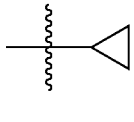 [SMILES: *C1CC1] | 0.15 ± 0.034 |
| ix | 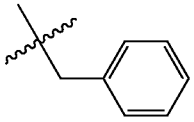 | | 0.209 ± 0.077 |

TABLE 3-continued

Biochemical inhibition of 7 in the HIV-1 integrase strand transfer assay

*Structure of compound 7: a pyrimidine core with N-hydroxy, two carbonyls, a carboxamide bearing NHR², and an NHR¹ substituent.*

| Compound (7-) | R¹ | R² | INST IC$_{50}$ (μM) |
|---|---|---|---|
| x | *tert*-butyl | benzyl | 0.081 ± 0.015 |
| xi | H | benzyl | 0.90 ± 0.29 |
| xii | CH$_3$ | 3-fluorobenzyl | 0.25 ± 0.048 |
| xiii | CH$_3$ | 4-fluorobenzyl | 0.11 ± 0.021 |
| xiv | CH$_3$ | 2-fluoro-3-chlorobenzyl | 0.11 ± 0.033 |
| xv | CH$_2$CH$_3$ | 3-fluorobenzyl | 0.068 ± 0.007 |
| xvi | CH$_2$CH$_3$ | 4-fluorobenzyl | 0.049 ± 0.004 |
| xvii | CH$_2$CH$_3$ | 2,5-difluorobenzyl | 0.068 ± 0.011 |

TABLE 3-continued
Biochemical inhibition of 7 in the HIV-1 integrase strand transfer assay
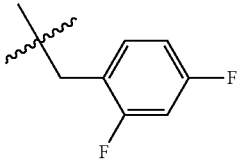 [SMILES: *Cc1ccc(F)cc1F]
7
| Compound (7-) | $R^1$ | $R^2$ | INST $IC_{50}$ (μM) |
|---|---|---|---|
| xviii | $CH_2CH_3$ | 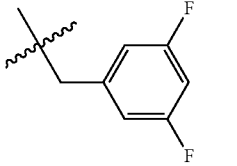 [SMILES: *Cc1cc(F)cc(F)c1] | 0.048 ± 0.007 |
| xix | $CH_2CH_3$ | 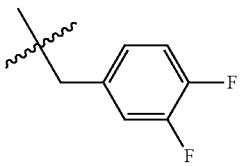 [SMILES: *Cc1ccc(F)c(F)c1] | 0.23 ± 0.062 |
| xx | $CH_2CH_3$ | 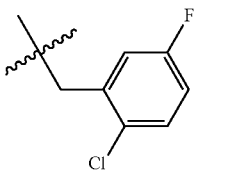 [SMILES: *Cc1cc(F)ccc1Cl] | 0.077 ± 0.011 |
| xxi | $CH_2CH_3$ | 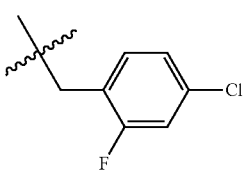 [SMILES: *Cc1ccc(Cl)cc1F] | 0.095 ± 0.019 |
| xxii | $CH_2CH_3$ | 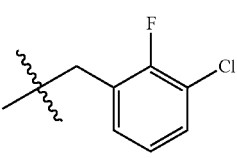 | 0.12 ± 0.021 |
| xxiii | $CH_2CH_3$ | 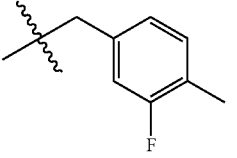 [SMILES: *Cc1ccc(C)c(F)c1] | 0.021 ± 0.002 |
| xxiv | $CH_2CH_3$ |  | 0.051 ± 0.013 |

TABLE 3-continued

Biochemical inhibition of 7 in the HIV-1 integrase strand transfer assay

[Structure of compound 7: pyrimidine core with HO-N, two C=O groups, C(=O)NH-R², NH-R¹ substituents]

7

| Compound (7-) | R¹ | R² | INST IC$_{50}$ (μM) |
|---|---|---|---|
| xxv | CH$_2$CH$_3$ | phenyl (direct attachment) | 35 ± 17 |
| xxvi | CH$_2$CH$_3$ | -CH$_2$CH$_2$-phenyl | 0.10 ± 0.03 |
| xxvii | CH$_2$CH$_3$ | CH$_2$CH$_2$Cl | >100 |
| xviii | CH$_2$CH$_2$CH$_3$ | 2-F-3-Cl-benzyl | 0.058 ± 0.012 |

The ST assay results clearly indicate a close correlation between the biochemical inhibition and antiviral activity. Amazingly all analogues that were highly active in the antiviral assay were found to inhibit INST in low nanomolar range, whereas none of the inactive compounds (7i-7iv, and 7xxvii) from the antiviral assay inhibited ST. Even for the active analogues, the most potent ones (7xxii, 7xx, 7xvii, 7xvi and 7vi) from antiviral assay (EC$_{50}$=15-61 nM, Table 2) also inhibited ST the best (IC$_{50}$=21-77 nM, Table 5). These observations strongly support the inhibition of INST as the mechanism of action for chemotype 7.

Mechanism of Strand Transfer Inhibition

HIV IN is a 32-kDa protein encoded by viral pol gene consisting of three functional domains[30]: the N-terminal domain (NTD) with a conserved "HH-CC" zinc-binding motif; the catalytic core domain (CCD) containing the key D64-D116-E152 catalytic triad; and the C-terminal domain (CTD) important for DNA binding. Although crystal structures of each single domain as well as double domains had been reported;[31-33] detailed understanding on HIV INST catalysis and inhibition remained elusive until the disclosure of crystal structures of full-length IN and viral DNA complex (intasome) for a homologous prototype foamy virus (PFV).[34, 35] Homologous models[36, 37] constructed based on these PFV intasome crystal structures have provided valuable details into HIV INST mechanism of action and formed the basis for structure-based INSTI design. Significantly these models corroborate the minimal pharmacophore embedded in major INSTIs as shown in FIG. 1.

Figure 2:
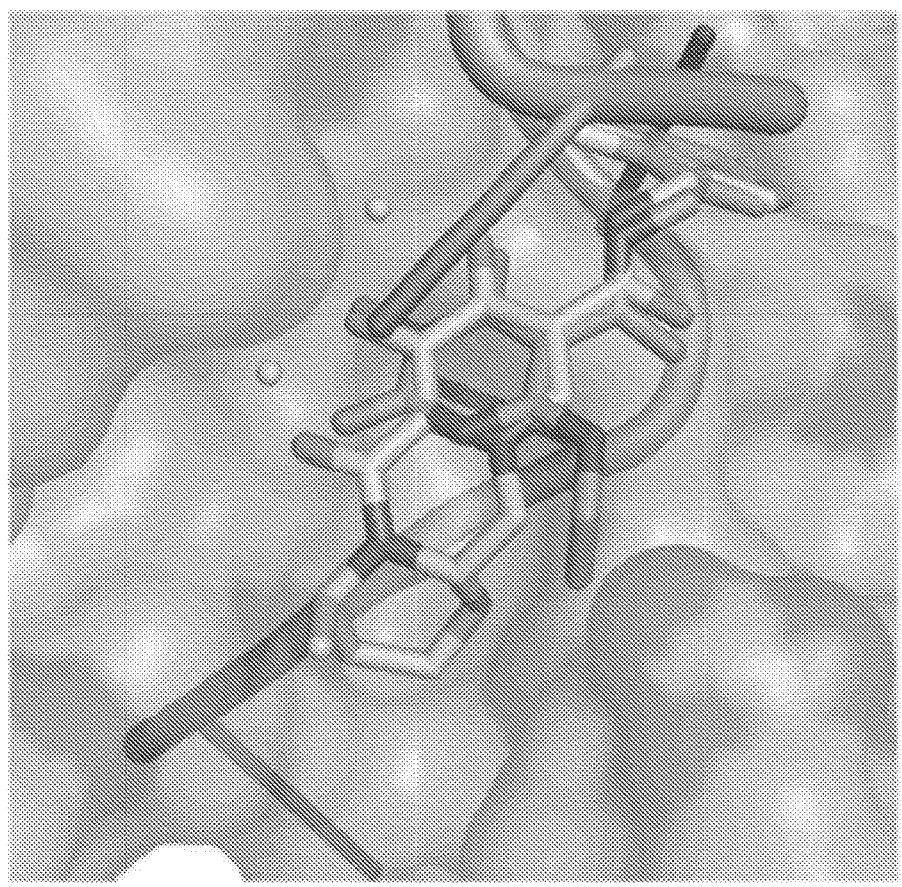
FIG. 2 shows docking of dolutegravir (11, orange) and inhibitor 7-xvi (cyan) in HIV-1 IN CCD in complex with $Mg^{2+}$ and DNA. The 3-N hydroxyl group simultaneously chelates to both $Mg^{2+}$ ions while allowing the placement of the benzyl group into the protein-DNA interfacial hydrophobic pocket.
Figure 3:
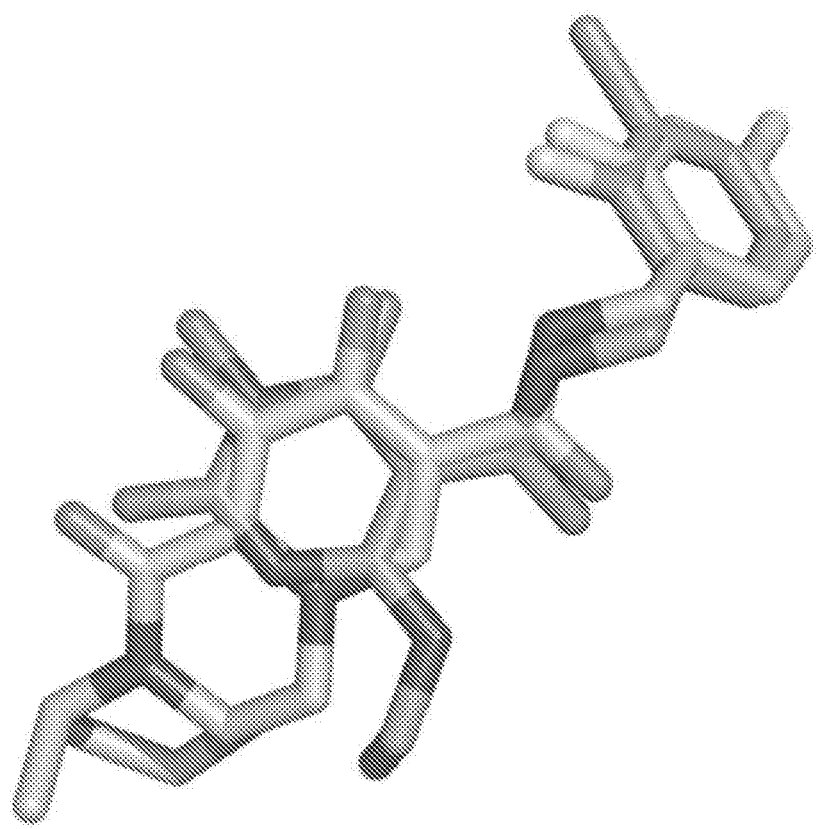
FIG. 3 shows a structural overlay of dolutegravir and a compound of formula (I) (inhibitor 7-xvi) of the invention.

FIG. 2 shows molecular docking on a representative analogue 7-xvi using a homologous HIV IN model.[36] Significantly, the new inhibitor 7-xvi fits perfectly into the IN binding site through two major binding domains also featured in DTG (11): the chelation of two Mg$^{2+}$ ions, and the placement of the 4-F-benzyl group into the protein-DNA interfacial hydrophobic pocket (FIG. 2). The high degree of similarity shown between the binding of 7-xvi and 11 confirms that the compounds of the various embodiments described herein can effectively engage with HIV IN to inhibit ST.

Resistance.

Mutations conferring resistance to INSTIs have been generated in cell culture and emerged in clinical studies.[38-40] To establish the resistance profile of chemotype 7, a representative compound 7xxiii was evaluated for antiviral potency against four RAL-resistant HIV-1 clones.[41] These clones contain one or more major mutations in HIV-1 IN that are associated with raltegravir resistance,[23, 24] namely a Y143C or an N155H single mutation; a G140S/Q148H double mutation and a G140S/Y143H/Q148H triple mutation. AZT and RAL were included in the study for comparison purpose. The results are summarized in Table 4. Obviously there is no cross-resistance for AZT due to a totally different mechanism of action. Interestingly compound 7-xxiii retains its potency against both single mutants (clones 1556-1 and 4736-2) while the double mutant (clone 8070-1) and the triple mutant (clone 8070-1) HIV-1 clones demonstrated moderate resistance to 7-xxiii, with a fold resistance of 13 and 6.3, respectively. These results suggest that chemotype 7 may confer antiviral activity via inhibiting INST, and that its binding mode to IN may be much similar to that of DTG (11), a second generation INSTI active against RAL-resistant HIV-1 strains.[42]

TABLE 4

Fold-resistance of 7-xxiii against raltegravir-resistant HIV-1 strains

| HIV-1 Clone | Major Mutations | Fold-resistance[a] | | |
|---|---|---|---|---|
| | | 7-xxiii[b] | AZT | RAL |
| 1556-1 | Y143C | 0.4 | 1.4 | 170 |
| 4736-2 | N155H | 2.4 | 0.7 | 14 |
| 8070-1 | G140S/Y143H/Q148H | 6.3 | 0.9 | 220 |
| 8070-2 | G140S/Q148H | 13 | 0.5 | 145 |

[a]Fold-resistance is defined by $EC_{50(mutant)}/EC_{50(WT)}$.

In Vitro Pharmacokinetics (PK)/ADME

To assess drug-like properties of chemotype 7, selected analogues were tested in various in vitro ADME studies (Table 5). Aqueous stability and solubility were evaluated in Dulbecco's Phosphate-Buffered Saline (DPBS). No degradation was observed with selected compounds in DPBS (37° C.) over a 24 h period with the exception of 7-xxii, which degraded slightly (86% remaining). In addition, all compounds were found to have good thermodynamic solubility in DPBS. Assessment of plasma and microsomal stability as well as plasma protein binding was done in two species, human and mouse. All compounds were found to be stable in both human and mouse plasma over 24 h at 37° C. However, these compounds showed a very high protein binding in human plasma (~99%). In mouse plasma, the protein binding was lower (70.9~95.9%). Microsomal stability of the compounds were evaluated in liver microsomes using either NADPH (phase I) or UDPGA (phase II) as cofactor. All the compounds were found to be stable against phase I NADPH-dependent metabolism but were subjected to fast phase II metabolic glucuronidation (Table 5).

TABLE 5

Physicochemical and in vitro ADME profile of selected analogues

| Compd | Aqueous Solubility (μM) | Aqueous Stability $t_{1/2}$ (h) | Plasma Stability $t_{1/2}$ (h) | | Plasma Protein Binding (%)[a] | | Microsomal Stability (Phase I/(Phase II, $CL_{int}$)[b] | |
|---|---|---|---|---|---|---|---|---|
| | | | Human | Mouse | Human | Mouse | Human | Mouse |
| 33 | 138 | >24 | >24 | >24 | 99.2 | 70.9 | 0.8/51 | <0.1/500 |
| 37 | 1091 | >24 | >24 | >24 | 99.1 | 83.9 | <0.1/355 | <0.1/732 |
| 45 | 150 | >24 | >24 | >24 | 99.4 | 86.5 | <0.1/336 | <0.1/1240 |
| 52 | 11 | >24 | >24 | >24 | 98.4 | 94.0 | <0.1/850 | <0.1/1065 |
| 53 | 81 | >24 | >24 | >24 | 98.9 | 95.9 | <0.1/357 | 0.4/1342 |

[a]Percent of fraction bound.
[b]$CL_{int}$: intrinsic clearance, μl/min/mg protein.

The compounds of the various embodiments described herein have a half maximal HIV-1 integrase strand transfer inhibitory concentration ($IC_{50}$) of from about 1 nM to about 250 μM (e.g., about 1 nM to about 250 nM, about 10 nM to about 100 nM, about 50 nM to about 300 nM, about 50 nM to about 500 nM, about 100 nM to about 800 nM or about 500 nM to about 10 μM).

In other embodiments, the compounds of the various embodiments described herein have a half maximal effective concentration ($EC_{50}$) of from about 1 nM to about 250 nM (e.g., about 10 nM to about 100 nM, about 50 nM to about 150 nM or about 50 nM to about 200 nM).

In still other embodiments, the compounds of the various embodiments described herein have a half maximal cytotoxic concentration ($CC_{50}$) of from about 10 μM to about 100 μM (e.g., about 10 μM to about 60 μM, about 25 μM to about 75 μM, about 10 μM to about 30 μM, about 50 μM to about 100 μM or about 15 μM to about 40 μM).

In still other embodiments, the compounds of the various embodiments described herein have a therapeutic index of from about 70 to about 2000 (e.g., about 100 to about 1000, about 70 to about 300, about 100 to about 500, about 500 to about 1500 or about 100 to about 1000).

In still other embodiments, the compounds of the various embodiments described herein have a CPE reduction %, which is indicative of anti-HIV-1 activity, of from about 30 to about 100% (e.g., about 50 to about 100%, about 60 to about 98, about 80 to about 98, about 90 to about 100% or about 91 to about 99%).

In yet other embodiments, the compounds of the various embodiments described herein have at least one of the following pharmacokinetic factors following, e.g., ip administration of a pharmaceutical composition comprising one or more of the compounds of the various embodiments described herein: a $T_{1/2}$ of from about 50 to 100 minutes; a $C_{max}$ of from about 250 to about 1000 μM; an AUC of from about 15,000 to about 50,000 min*μM; a V of from about 1 to about 1.5 L/kg; or a CL of from about 0.05 to about 0.2 L/min/kg.

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials. All commercially available chemicals were obtained from Aldrich, Alfa Aesare, Wako, Acros, Fisher, Fluka, Maybridge or the like and were used without further purification, except where noted. Dry solvents are obtained, for example, by passing these through activated alumina columns.

The present invention further embraces isolated compounds of the invention. The expression "isolated compound" refers to a preparation of a compound of the invention, or a mixture of compounds the invention, wherein the isolated compound has been separated from the reagents used, and/or byproducts formed, in the synthesis of the compound or compounds. "Isolated" does not mean that the preparation is technically pure (homogeneous), but it is sufficiently pure to compound in a form in which it can be used therapeutically. Preferably an "isolated compound" refers to a preparation of a compound of the invention or a mixture of compounds of the invention, which contains the named compound or mixture of compounds of the invention in an amount of at least 10 percent by weight of the total weight. Preferably the preparation contains the named compound or mixture of compounds in an amount of at least 50 percent by weight of the total weight; more preferably at least 80 percent by weight of the total weight; and most preferably at least 90 percent, at least 95 percent or at least 98 percent by weight of the total weight of the preparation.

The compounds of the invention and intermediates may be isolated from their reaction mixtures and purified by standard techniques such as filtration, liquid-liquid extraction, solid phase extraction, distillation, recrystallization or chromatography, including flash column chromatography, or HPLC.

Another aspect of an embodiment of the invention provides compositions of the compounds of the invention, alone or in combination with another medicament. As set forth herein, compounds of the invention include stereoisomers, tautomers, solvates, prodrugs, pharmaceutically acceptable salts and mixtures thereof. Compositions containing a compound of the invention can be prepared by conventional techniques, e.g. as described in Remington: *The Science and Practice of Pharmacy,* 19th Ed., 1995, or later versions thereof, incorporated by reference herein. The compositions can appear in conventional forms, for example capsules, tablets, aerosols, solutions, suspensions or topical applications.

Typical compositions include a compound of the invention and a pharmaceutically acceptable excipient which can be a carrier or a diluent. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent can include any sustained release material known in the art, such as glyceryl monostearate or glyceryl distearate, alone or mixed with a wax.

The formulations can be mixed with auxiliary agents which do not deleteriously react with the active compounds. Such additives can include wetting agents, emulsifying and suspending agents, salt for influencing osmotic pressure, buffers and/or coloring substances preserving agents, sweetening agents or flavoring agents. The compositions can also be sterilized if desired.

The route of administration can be any route which effectively transports the active compound of the invention to the appropriate or desired site of action, such as oral, nasal, pulmonary, buccal, subdermal, intradermal, transdermal or parenteral, e.g., rectal, depot, subcutaneous, intravenous, intraurethral, intramuscular, intranasal, ophthalmic solution or an ointment, the oral route being preferred.

If a solid carrier is used for oral administration, the preparation can be tableted, placed in a hard gelatin capsule in powder or pellet form or it can be in the form of a troche or lozenge. If a liquid carrier is used, the preparation can be in the form of a syrup, emulsion, soft gelatin capsule or sterile injectable liquid such as an aqueous or non-aqueous liquid suspension or solution.

Injectable dosage forms generally include aqueous suspensions or oil suspensions which can be prepared using a suitable dispersant or wetting agent and a suspending agent Injectable forms can be in solution phase or in the form of a suspension, which is prepared with a solvent or diluent. Acceptable solvents or vehicles include sterilized water. Ringer's solution, or an isotonic aqueous saline solution. Alternatively, sterile oils can be employed as solvents or suspending agents. Preferably, the oil or fatty acid is non-volatile, including natural or synthetic oils, fatty acids, mono-, di- or tri-glycerides.

For injection, the formulation can also be a powder suitable for reconstitution with an appropriate solution as described above. Examples of these include, but are not limited to, freeze dried, rotary dried or spray dried powders, amorphous powders, granules, precipitates, or particulates. For injection, the formulations can optionally contain stabilizers, pH modifiers, surfactants, bioavailability modifiers and combinations of these. The compounds can be formulated for parenteral administration by injection such as by bolus injection or continuous infusion. A unit dosage form for injection can be in ampoules or in multi-dose containers.

The formulations of the invention can be designed to provide quick, sustained, or delayed release of the active ingredient after administration to the patient by employing procedures well known in the art. Thus, the formulations can also be formulated for controlled release or for slow release.

Compositions contemplated by the present invention can include, for example, micelles or liposomes, or some other encapsulated form, or can be administered in an extended release form to provide a prolonged storage and/or delivery effect. Therefore, the formulations can be compressed into pellets or cylinders and implanted intramuscularly or subcutaneously as depot injections. Such implants can employ known inert materials such as silicones and biodegradable polymers, e.g., polylactide-polyglycolide. Examples of other biodegradable polymers include poly(orthoesters) and poly(anhydrides).

Generally, the compounds of the invention are dispensed in unit dosage form including from about 0.05 mg to about 1000 mg of active ingredient together with a pharmaceutically acceptable carrier per unit dosage.

Usually, dosage forms suitable for oral, nasal, pulmonal or transdermal administration include from about 125 µg to about 1250 mg, preferably from about 250 µg to about 500 mg, and more preferably from about 2.5 mg to about 250 mg, of the compounds admixed with a pharmaceutically acceptable carrier or diluent.

Dosage forms can be administered daily, or more than once a day, such as twice or thrice daily. Alternatively dosage forms can be administered less frequently than daily, such as every other day, or weekly, if found to be advisable by a prescribing physician.

It is within ordinary skill to evaluate any compound disclosed and claimed herein for effectiveness in inhibition of HIV integrase and in the various cellular assays for effectiveness in the treatment of AIDS, using the procedures described above or found in the scientific literature. Accordingly, the person of ordinary skill can prepare and evaluate any of the claimed compounds without undue experimentation.

Any compound found to be an effective inhibitor of HIV can likewise be tested in animal models and in human clinical studies using the skill and experience of the investigator to guide the selection of dosages and treatment regimens for the treatment of AIDS.

EXAMPLES

Chemistry
General Procedures.

All commercial chemicals were used as supplied unless otherwise indicated. Dry solvents were either purchased (toluene and MeOH) or dispensed under argon from an anhydrous solvent system with two packed columns of neutral alumina or molecular sieves. Flash chromatography was performed on a Teledyne Combiflash RF-200 with RediSep columns (silica) and indicated mobile phase. All moisture sensitive reactions were performed under an inert atmosphere of ultra-pure argon with oven-dried glassware. $^1$H and $^{13}$C NMR spectra were recorded on a Varian 600 MHz spectrometer. Mass data were acquired on an Agilent TOF II TOS/MS spectrometer capable of ESI and APCI ion sources. Analysis of sample purity was performed on a Varian Prepstar SD-1 HPLC system with a Phenomenex Gemini, 5 micron C18 column (250 mm×4.6 mm). HPLC conditions: solvent A=$H_2O$ containing 0.1% TFA, solvent B=MeCN; flow rate=1.0 mL/min; compounds were eluted with a gradient of 20% MeCN/$H_2O$ to 100% MeCN for 30 min. Purity was determined by total absorbance at 254 nm. All tested compounds have a purity ≥96.

Procedure b for Preparation of
3-(benzyloxy)-6-hydroxypyrimidine-2,4(1H,3H)-dione
2 under Microwave Irradiation To a 20 mL-type microwave reaction vessel were added 1-(benzyloxy)urea 1 (1 g, 6.02 mmol), freshly made sodium ethoxide (6.02 mmol, 1 eq) in 5.5 mL of anhydrous Ethanol and Diethyl malonate (6.02 mmol, 1 eq). The reaction vessel was irradiated at 150° C. for 20 min. The reaction mixture was transferred to a round-bottomed flask and removed solvent under reduced pressure. The residue was dissolved in water, then treated with 1 N aqueous HCl to adjust the PH 4~5. The precipitate was filtered off, washed with cold DCM and small amount of MeOH, and Et$_2$O, and finally dried in vacuo to give compound 3-(benzyloxy)-6-hydroxypyrimidine-2,4(1H,3H)-dione 2 as a light yellow solid in 58% yield.

Procedure c for Preparation of Compound
3-(benzyloxy)-6-chloropyrimidine-2,4(1H,3H)-dione
3

To a solution of 3-(benzyloxy)-6-hydroxypyrimidine-2,4 (1H,3H)-dione 2 (10 g, 42.7 mmol) in POCl$_3$ (40 mL) was added BnEt$_3$NCl (85.4 mmol, 2.0 equiv.) and the mixture was stirred at 50° C. temperature for 6 h. The reaction mixture was cool down to mom temperature and then pour it onto the ice. The precipitate was filtered off, washed sequentially by water. MeOH and EtOEt and finally dried in vacuo to give compound 3-(benzyloxy)-6-chloropyrimidine-2,4(1H,3H)-dione 3 as a light yellow solid in 88% yield.

Procedure d for 6-Amination Product 5 Under
Microwave Irradiation

To a microwave reaction vessel were added compound 3-(benzyloxy)-6-chloropyrimidine-2,4(1H,3H)-dione 4 (1 mmol), alkyl amine (3 mmol, 3 eq) and N,N-dimethylaniline (2 mmol, 2 eq). The reaction vessel was irradiated at 170° C. for appropriate time. The reaction was monitored by both TLC and LC-MS. The reaction mixture was transferred to a round-bottomed flask and concentrated under reduced pressure. The residue was purified by flash chromatography on silica gel (DCM-MeOH) or recrystallization (MeOH) to provide the desired compound 5 as a solid in 54-78%.

General Procedure e for 5-Carbamoylation Product
6 Under Microwave Irradiation

To a microwave reaction vessel were added 6-amino-3-(benzyloxy)-pyrimidine-2,4(1H,3H)-dione 5 (1 mmol), isocyanate or acylazide (1.2 mmol) and nitrobenzene (1 mL). The reaction vessel was irradiated at 210° C. for the appropriate time. The reaction was monitored by both TLC and LC-MS. The reaction mixture was either purified by flash chromatography on silica gel (EtOAc-hexane) or recrystallization (MeOH) to provide the corresponding carbamoylated 6-amino-3-(benzyloxy)-pyrimidine-2,4(1H,3H)-dione 6 as a solid in 60%-100%.

General Procedure f for a Two-Step Conventional
5-Carbamoylation of 5

To an ice-cooled solution of 6-amino-3-(benzyloxy)-pyrimidine-2,4(1H,3H)-dione 5 (380 mg, 1.45 mmol) in pyridine (5 mL), phenyl chloroformate (226 µL, 1.75 mmol, 1.2 eq) was added and the mixture was stirred at rt for 2 h. Pyridine was removed by evaporation and residue was solidified by mixing with ether. Solid was collected by filtration, washed with MeOH and ether, and dried in vacuo to give intermediate phenyl ester (305 mg, 55%) as a white solid; ii) intermediate phenyl ester (100 mg, 0.26 mmol) and amine (2.6 mmol, 10 eq) were mixed in anhydrous THF or dioxane (2.6 mL) in a microwave reactor and heated under microwave condition at 100° C. for 50 min. The reaction was monitored by TLC plate and LC-MS. The reaction mixture was transferred to a round-bottomed flask and concentrated under reduced pressure. The residue was purified by flash chromatography on silica gel (DCM-MeOH) or recrystallization (MeOH) to provide the desired compound 6 as a solid in 80-92%.

General Procedure g for Pd/C Catalyzed
Hydrogenolysis Debenzylation Products 7

To a solution of 100 mg of 6-amino-3-(benzyloxy)-5-carbamoyl-pyrimidine-2,4(1H,3H)-dione 6 in 7.0 mL MeOH was added 20 mg Pearlman's catalyst (Pd—C, 20%). The reaction mixture was degassed using vacuum and refilling with $H_2$ (40-50 psi) for three times. Then keep the reaction mixture being shaked under a $H_2$ (40-50 psi) atmosphere for appropriate time. The reaction was monitored by both TLC and LC-MS. The reaction mixture was filtered through a short celite column and then removed the solvent. Trituration with MeOH, ethyl acetate and DCM provided desired final compounds 7 in 82-97% yield.

General Procedure h for TFA-Mediated Debenzylation Products 7 Under Microwave Irradiation To a microwave reaction vessel were added 6-amino-3-(benzyloxy)-5-carbamoyl-pyrimidine-2,4(1H,3H)-dione 6 (0.26 mmol), TFA (6~10 mL). The reaction vessel was irradiated at 120° C. for the appropriate time. The reaction was monitored by both TLC and LC-MS. The reaction mixture was transferred to a round-bottom flask to remove the solvent under reduced pressure. Then the residue was purified by flash chromatography on C18 reverse phase column ($H_2O$-MeOH) or trituration (MeOH, Ethylacetate and DCM) to provide the desired compounds 7 as a solid in 50-77%.

1-(Benzyloxy)urea (2)

White solid, 91% yield; $^1$H NMR (600 MHz, DMSO-$d_6$): δ 9.00 (s, 1H), 7.41-7.36 (m, 5H), 6.33 (s, 2H), 4.71 (s, 2H); $^{13}$C NMR (150 MHz, DMSO-$d_6$): δ 160.7, 136.6, 128.7, 128.2, 127.9, 77.2.

3-(Benzyloxy)-6-hydroxypyrimidine-2,4(1H,3H)-dione (3)

Light yellow solid, 58% yield; $^1$H NMR (600 MHz, DMSO-d6): δ 11.50 (s, 1H), 7.52-7.40 (m, 5H), 4.96 (s, 2H), 3.73 (s, 2H); $^{13}$C NMR (150 MHz, DMSO-d6): δ 165.9, 162.5, 148.7, 134.4, 129.4, 128.9, 128.4, 77.6, 41.1.

3-(Benzyloxy)-6-chloropyrimidine-2,4(1H,3H)-dione (4)

Light yellow solid, 88% yield; $^1$H NMR (600 MHz, DMSO-$d_6$): δ 12.60 (s, 1H), 7.52-7.39 (m, 5H), 5.99 (s, 1H), 5.01 (s, 2H); $^{13}$C NMR (150 MHz, DMSO-$d_6$): δ 158.5, 148.1, 142.9, 134.3, 129.5, 128.9, 128.4, 99.9, 77.3.

3-(Benzyloxy)-6-(phenylamino)pyrimidine-2,4(1H,3H)-dione (5-i)

White solid, 54% yield; $^1$H NMR (600 MHz, DMSO-$d_6$): δ 10.81 (s, 1H), 8.34 (s, 1H), 7.53-7.19 (m, 10H), 4.98 (s, 2H), 4.78 (s, 1H); $^{13}$C NMR (150 MHz, DMSO-$d_6$): δ 159.9, 150.4, 148.5, 137.8, 134.6, 129.4, 129.3, 128.7, 128.3, 124.9, 123.0, 77.2, 75.7.

3-(Benzyloxy)-6-(biphenyl amino)pyrimidine-2,4(1H,3H)-dione (5-ii)

Off white solid, 81% yield; 1H NMR (600 MHz, DMSO-d6): δ 10.86 (s, 1H), 8.48 (s, 1H), 7.71-7.30 (m, 14H), 5.00 (s, 2H), 4.89 (s, 1H); 13C NMR (150 MHz, DMSO-d6): δ 160.0, 150.2, 148.5, 139.4, 137.3, 136.4, 134.6, 129.3, 128.9, 128.7, 128.3, 127.6, 127.3, 126.4, 123.0, 77.3, 76.2.

3-(Benzyloxy)-6-(methylamino)pyrimidine-2,4(1H,3H)-dione (5-v)

White solid, 77% yield; $^1$H NMR (600 MHz, DMSO-$d_6$): δ 10.67 (s, 1H), 7.52-7.37 (m, 5H), 6.12 (brs, 1H), 4.95 (s, 2H), 4.51 (s, 1H); 2.65 (d, J=4.8 Hz, 3H); $^{13}$C NMR (150 MHz, DMSO-$d_6$): δ 159.9, 152.9, 148.5, 134.8, 129.3, 128.6, 128.2, 77.2, 72.1, 28.5.

3-(Benzyloxy)-6-(ethylamino)pyrimidine-2,4(1H,3H)-dione (5-vi)

White solid, 79% yield; $^1$H NMR (600 MHz, DMSO-$d_6$): δ 10.43 (s, 1H), 7.51-7.37 (m, 5H), 6.11 (brs, 1H), 4.95 (s, 2H), 4.56 (brs, 1H); 2.65 (dq, J=6.0, 6.6 Hz, 2H), 2.65 (t, J=6.6 Hz, 3H); $^{13}$C NMR (150 MHz, DMSO-$d_6$): δ 159.9, 151.9, 148.5, 134.7, 129.3, 128.6, 128.2, 77.2, 72.2, 36.3, 13.8.

3-(Benzyloxy)-6-(propylamino)pyrimidine-2,4(1H,3H)-dione (5-vii)

White solid, 72% yield; $^1$H NMR (600 MHz, DMSO-$d_6$): δ 10.38 (s, 1H), 7.51-7.38 (m, 5H), 6.15 (brs, 1H), 4.95 (s, 2H), 4.57 (s, 1H); 2.98 (m, 2H), 1.50 (m, 2H), 0.88 (t, J=7.2 Hz, 3H); $^{13}$C NMR (150 MHz, DMSO-$d_6$): δ 159.9, 152.1, 148.4, 134.8, 129.3, 128.6, 128.2, 77.2, 72.2, 43.1, 21.4, 11.1.

3-(Benzyloxy)-6-(isopropylamino)pyrimidine-2,4(1H,3H)-dione (5-viii)

White solid, 34% yield; $^1$H NMR (600 MHz, DMSO-$d_6$): δ 10.19 (s, 1H), 7.51-7.37 (m, 5H), 5.99 (d, J=6.0 Hz, 1H), 4.94 (s, 2H), 4.59 (s, 1H); 3.54 (m, 1H), 1.12 (d, J=6.0 Hz, 6H); $^{13}$C NMR (150 MHz, DMSO-$d_6$): δ 159.9, 151.1, 148.4, 134.7, 129.30, 129.26, 128.6, 128.3, 128.2, 77.2, 72.5, 43.2, 22.0.

3-(Benzyloxy)-6-(cyclopropylamino)pyrimidine-2,4(1H,3H)-dione (5-ix)

White solid, 38% yield; $^1$H NMR (600 MHz, DMSO-$d_6$): δ 10.44 (s, 1H), 7.51-7.38 (m, 5H), 6.49 (s, 1H), 4.94 (s, 2H), 4.78 (s, 1H); 2.40 (m, 1H), 0.73 (m, 2H), 0.48 (m, 2H); $^{13}$C NMR (150 MHz, DMSO-$d_6$): δ 159.8, 153.2, 148.4, 134.7, 129.30, 128.7, 128.3, 77.2, 73.8, 23.4, 6.7.

6-(tert-Butylamino)-3-(benzyloxy)pyrimidine-2,4(1H,3H)-dione (5-x)

White solid, 27% yield; $^1$H NMR (600 MHz, DMSO-$d_6$): δ 9.95 (s, 1H), 7.51-7.38 (m, 5H), 5.88 (s, 1H), 4.95 (s, 2H), 467 (s, 1H); 1.30 (s, 9H); $^{13}$C NMR (150 MHz, DMSO-$d_6$): δ 159.8, 150.0, 148.3, 134.7, 129.3, 128.6, 128.2, 77.3, 74.6, 50.9, 28.4.

N-Benzyl-1-(benzyloxy)-1,2,3,6-tetrahydro-2,6-dioxo-4-(phenylamino)pyrimidine-5-carboxamide (6-i)

White solid, 84% yield; $^1$H NMR (600 MHz, DMSO-$d_6$): δ 12.84 (s, 1H), 11.46 (s, 1H), 9.95 (s, 1H), 7.54-7.27 (m, 15H), 5.02 (d, J=3.0, 2H), 4.50 (s, 2H); $^{13}$C NMR (150 MHz, DMSO-$d_6$): δ 167.6, 160.9, 154.5, 146.5, 139.3, 135.7, 134.5, 129.6, 129.3, 128.8, 128.4, 128.3, 127.4, 126.9, 126.6, 125.0, 81.0, 77.4, 41.9; HRMS-ESI(−) m/z calcd for $C_{25}H_{22}N_4O_4$ 441.1568 [M−H]$^-$, found 441.1579.

N-Benzyl-1-(benzyloxy)-1,2,3,6-tetrahydro-2,6-dioxo-4-(biphenylamino)pyrimidine-5-carboxamide (6-ii)

White solid, 70% yield; $^1$H NMR (600 MHz, DMSO-d$_6$): δ 12.88 (s, 1H), 11.54 (s, 1H), 9.96 (t, J=6.0, 1H), 7.54-7.26 (m, 19H), 5.03 (s, 2H), 4.51 (d, J=6.0, 2H); $^{13}$C NMR (150 MHz, DMSO-d$_6$): δ 167.6, 160.9, 154.6, 146.6, 139.3, 138.2, 135.1, 134.5, 129.3, 129.0, 128.8, 128.4, 128.3, 128.2, 127.7, 127.5, 127.4, 126.9, 126.5, 125.5, 81.2, 77.5, 42.0; HRMS-ESI(−) m/z calcd for $C_{31}H_{26}N_4O_4$ 517.1881 [M−H]$^-$, found 517.1910.

N-(3-Fluorobenzyl)-1-(benzyloxy)-1,2,3,6-tetrahydro-2,6-dioxo-4-(biphenylamino)pyrimidine-5-carboxamide (6-iii)

White solid, 92% yield; $^1$H NMR (600 MHz, DMSO-d$_6$): δ 12.81 (s, 1H), 11.50 (s, 1H), 10.01 (t, J=6.0, 1H), 7.75-7.07 (m, 18H), 5.04 (s, 2H), 4.53 (d, J=6.0, 2H); $^{13}$C NMR (150 MHz, DMSO-d$_6$): δ 167.7, 162.2 (d, $J_{CF}$=241.8 Hz), 160.9, 154.6, 146.6, 142.6 (d, $J_{CF}$=6.5 Hz), 139.3, 138.3, 135.1, 134.5, 130.3 (d, $J_{CF}$=7.7 Hz), 129.3, 129.0, 128.8, 128.3, 127.7, 127.5, 126.5, 125.5, 123.3 (d, $J_{CF}$=3.3 Hz), 114.0 (d, $J_{CF}$=21.6 Hz), 113.6 (d, $J_{CF}$=20.7 Hz), 81.1, 77.5, 41.5.

N-(4-Fluorobenzyl)-1-(benzyloxy)-1,2,3,6-tetrahydro-2,6-dioxo-4-(biphenylamino)pyrimidine-5-carboxamide (6-iv)

White solid, 96% yield; $^1$H NMR (600 MHz, DMSO-d$_6$): δ 12.85 (s, 1H), 11.54 (s, 1H), 9.97 (t, J=6.0, 1H), 7.75-7.16 (m, 18H), 5.03 (s, 2H), 4.49 (d, J=6.0, 2H); $^{13}$C NMR (150 MHz, DMSO-d$_6$): δ 167.6, 161.2 (d, $J_{CF}$=240.8 Hz), 160.9, 154.5, 146.6, 139.3, 138.3, 135.6 (d, $J_{CF}$=3.5 Hz), 135.1, 134.5, 129.4 (d, $J_{CF}$=7.7 Hz), 129.3, 129.0, 128.8, 128.3, 127.7, 127.5, 126.5, 125.5, 115.1 (d, $J_{CF}$=21.6 Hz), 81.1, 77.5, 41.2.

N-Benzyl-1-(benzyloxy)-1,2,3,6-tetrahydro-4-(methylamino)-2,6-dioxopyrimidine-5-carboxamide (6-v)

White solid, 77% yield; $^1$H NMR (600 MHz, DMSO-d$_6$): δ 11.20 (s, 1H), 11.02 (q, J=4.8 Hz, 1H), 9.82 (t, J=6.0 Hz, 1H), 7.53-7.24 (m, 10H), 5.00 (s, 2H), 4.44 (d, J=6.0 Hz, 2H); 2.96 (d, J=5.4 Hz, 3H); $^{13}$C NMR (150 MHz, DMSO-d$_6$): δ 167.6, 160.5, 156.1, 146.9, 139.6, 134.5, 129.3, 128.7, 128.34, 128.29, 127.3, 126.8, 79.2, 77.4, 41.8, 28.5.

N-Benzyl-1-(benzyloxy)-4-(ethylamino)-1,2,3,6-tetrahydro-2,6-dioxopyrimidine-5-carboxamide (6-vi)

White solid, 77% yield; $^1$H NMR (600 MHz, DMSO-d$_6$): δ 11.24 (s, 1H), 11.19 (t, J=5.4 Hz, 1H), 9.85 (t, J=6.0 Hz, 1H), 7.53-7.24 (m, 10H), 5.00 (s, 2H), 4.44 (d, J=6.0 Hz, 2H), 3.39 (m, 2H), 1.16 (t, J=6.6 Hz, 3H); $^{13}$C NMR (150 MHz, DMSO-d$_6$): δ 167.7, 160.6, 155.1, 146.9, 139.6, 134.5, 129.3, 128.7, 128.4, 128.3, 127.3, 126.8, 79.0, 77.4, 41.8, 36.2, 14.4.

N-Benzyl-1-(benzyloxy)-1,2,3,6-tetrahydro-2,6-dioxo-4-(propylamino)pyrimidine-5-carboxamide (6-vii)

White solid, 74% yield; $^1$H NMR (600 MHz, DMSO-d$_6$): δ 11.30 (s, 1H), 11.27 (s, 1H), 9.86 (t, J=6.0 Hz, 1H), 7.52-7.25 (m, 10H), 5.00 (s, 2H), 4.45 (s, 2H); 3.32 (m, 2H), 1.55 (m, 2H), 0.92 (t, J=6.6 Hz, 3H); $^{13}$C NMR (150 MHz, DMSO-d$_6$): δ 167.8, 160.6, 155.3, 146.8, 139.5, 134.5, 129.3, 128.7, 128.4, 128.3, 127.3, 126.8, 79.0, 77.4, 42.8, 41.8, 22.1, 11.0.

N-Benzyl-1-(benzyloxy)-1,2,3,6-tetrahydro-4-(isopropylamino)-2,6-dioxopyrimidine-5-carboxamide (6-viii)

White solid, 53% yield; $^1$H NMR (600 MHz, DMSO-d$_6$): δ 11.32 (d, J=8.4, 1H), 11.26 (s, 1H), 9.89 (t, J=6.0, 1H), 7.53-7.24 (m, 10H), 5.00 (s, 2H), 4.44 (d, J=6.0, 2H); 4.11 (m, 1H), 1.18 (d, J=6.6 Hz, 6H); $^{13}$C NMR (150 MHz, DMSO-d$_6$): δ 167.9, 160.8, 154.2, 147.0, 139.6, 134.6, 129.4, 128.9, 128.5, 128.4, 127.4, 127.0, 79.0, 77.6, 42.9, 41.9, 22.9.

N-Benzyl-1-(benzyloxy)-4-(cyclopropylamino)-1,2,3,6-tetrahydro-2,6-dioxopyrimidine-5-carboxamide (6-ix)

White solid, 20% yield; $^1$H NMR (600 MHz, DMSO-d$_6$): δ 11.34 (s, 1H), 11.17 (s, 1H), 9.80 (t, J=6.0, 1H), 7.53-7.23 (m, 10H), 5.00 (s, 2H), 4.42 (d, J=5.4, 2H); 2.75 (m, 1H), 0.86 (m, 2H), 0.63 (s, 2H); $^{13}$C NMR (150 MHz, DMSO-d$_6$): δ 167.5, 160.5, 157.0, 146.7, 139.5, 134.5, 129.4, 128.8, 128.42, 128.36, 127.3, 126.9, 79.4, 77.5, 41.8, 23.2, 7.8.

4-(tert-Butylamino)-N-benzyl-1-(benzyloxy)-1,2,3,6-tetrahydro-2,6-dioxopyrimidine-5-carboxamide (6-x)

White solid, 22% yield; $^1$H NMR (600 MHz, DMSO-d$_6$): δ 11.98 (s, 1H), 10.15 (brs, 1H), 10.02 (t, J=6.0 Hz, 1H), 7.53-7.25 (m, 10H), 5.01 (s, 2H), 4.44 (d, J=5.4 Hz, 2H), 1.43 (s, 9H); $^{13}$C NMR (150 MHz, DMSO-d$_6$): δ 168.0, 160.7, 154.1, 146.4, 139.5, 134.5, 129.3, 128.8, 128.4, 128.3, 127.3, 126.9, 79.1, 77.5, 52.2, 41.8, 29.0.

4-Amino-N-benzyl-1-(benzyloxy)-1,2,3,6-tetrahydro-2,6-dioxopyrimidine-5-carboxamide (6-xi)

White solid, 23% yield; $^1$H NMR (600 MHz, DMSO-d$_6$): δ 11.26 (s, 1H), 9.84 (brs, 1H), 9.66 (t, J=6.0 Hz, 1H), 7.52-7.25 (m, 9H), 6.89 (s, 1H), 4.99 (s, 2H), 4.44 (d, J=5.4 Hz, 2H); $^{13}$C NMR (150 MHz, DMSO-d$_6$): δ 166.8, 161.0, 156.3, 146.4, 139.6, 134.5, 129.3, 128.8, 128.4, 128.3, 127.3, 126.8, 80.0, 77.5, 41.7.

N-(3-Fluorobenzyl)-1-(benzyloxy)-1,2,3,6-tetrahydro-4-(methylamino)-2,6-dioxopyrimidine-5-carboxamide (6-xii)

White solid, 43% yield; $^1$H NMR (600 MHz, DMSO-d$_6$): δ 11.21 (s, 1H), 10.96 (q, J=5.4 Hz, 1H), 9.86 (dd, J=6.0, 5.4 Hz, 1H), 7.54-7.06 (m, 9H), 5.01 (s, 2H), 4.45 (d, J=5.4 Hz, 2H), 2.96 (d, J=5.4 Hz, 3H); $^{13}$C NMR (150 MHz, DMSO-d$_6$): δ 167.7, 162.2 (d, $J_{CF}$=241.5 Hz), 160.5, 156.1, 146.9, 142.9 (d, $J_{CF}$=6.9 Hz), 134.5, 130.2 (d, $J_{CF}$=8.0 Hz), 129.3, 128.8, 128.3, 123.2 (d, $J_{CF}$=3.5 Hz), 113.4 (d, $J_{CF}$=21.8 Hz), 113.4 (d, $J_{CF}$=20.7 Hz), 79.2, 77.4, 41.3, 28.5.

N-(4-Fluorobenzyl)-1-(benzyloxy)-1,2,3,6-tetrahydro-4-(methylamino)-2,6-dioxopyrimidine-5-carboxamide (6-xiii)

White solid, 58% yield; $^1$H NMR (600 MHz, DMSO-d$_6$): δ 11.20 (s, 1H), 11.00 (q, J=5.4 Hz, 1H), 9.82 (t, J=6.0 Hz, 1H), 7.53-7.13 (m, 9H), 5.00 (s, 2H), 4.41 (d, J=6.0 Hz, 2H), 2.96 (d, J=5.4 Hz, 3H); $^{13}$C NMR (150 MHz, DMSO-d$_6$): δ 167.6, 161.1 (d, $J_{CF}$=240.3 Hz), 160.5, 156.1, 146.8, 136.0 (d, $J_{CF}$=3.5 Hz), 134.5, 129.34, 129.32 (d, $J_{CF}$=8.1 Hz), 128.8, 128.3, 115.0 (d, $J_{CF}$=20.7 Hz), 79.2, 77.5, 41.0, 28.5.

N-(3-Chloro-2-fluorobenzyl)-1-(benzyloxy)-1,2,3,6-tetrahydro-4-(methylamino)-2,6-dioxopyrimidine-5-carboxamide (6-xiv)

White solid, 64% yield; $^1$H NMR (600 MHz, DMSO-d$_6$): δ 11.21 (s, 1H), 10.88 (q, J=4.8 Hz, 1H), 9.87 (t, J=6.0 Hz, 1H), 7.54-7.18 (m, 8H), 5.02 (s, 2H), 4.51 (d, J=4.8 Hz, 2H), 2.95 (d, J=4.8 Hz, 3H); $^{13}$C NMR (150 MHz, DMSO-d$_6$): δ 167.7, 160.5, 156.1, 155.2 (d, $J_{CF}$=245 Hz), 146.8, 134.5, 129.4 129.1, 28.8, 128.6 (d, $J_{CF}$=15.0 Hz), 128.33 (d, $J_{CF}$=3.4 Hz), 128.32, 125.2 (d, $J_{CF}$=4.7 Hz), 119.4 (d, $J_{CF}$=17.3 Hz), 79.0, 77.5, 35.8 (d, $J_{CF}$=4.5 Hz), 28.4.

N-(3-Fluorobenzyl)-1-(benzyloxy)-4-(ethylamino)-1,2,3,6-tetrahydro-2,6-dioxopyrimidine-5-carboxamide (6-xv)

White solid, 92% yield; $^1$H NMR (600 MHz, DMSO-d$_6$): δ 11.25 (s, 1H), 11.13 (t, J=5.4 Hz, 1H), 9.90 (L, J=6.0 Hz, 1H), 7.54-7.06 (m, 9H), 5.01 (s, 2H), 4.46 (d, J=6.0 Hz, 2H), 3.39 (td, J=7.2, 6.6 Hz, 2H), 1.15 (dd, J=7.2, 6.6 Hz, 3H); $^{13}$C NMR (150 MHz, DMSO-d$_6$): δ 167.8, 162.2 (d, $J_{CF}$=241.5 Hz), 160.6, 155.1, 146.8, 142.9 (d, $J_{CF}$=6.9 Hz), 134.5, 130.3 (d, $J_{CF}$=8.1 Hz), 129.3, 128.8, 128.3, 123.2 (d, $J_{CF}$=2.3 Hz), 138.9 (d, $J_{CF}$=21.8 Hz), 113.5 (d, $J_{CF}$=21.9 Hz), 79.0, 77.4, 41.3, 36.2, 14.4.

N-(4-Fluorobenzyl)-1-(benzyloxy)-4-(ethylamino)-1,2,3,6-tetrahydro-2,6-dioxopyrimidine-5-carboxamide (6-xvi)

White solid, 68% yield; $^1$H NMR (600 MHz, DMSO-d$_6$): δ 11.24 (s, 1H), 11.16 (t, J=5.4 Hz, 1H), 9.86 (t, J=6.0 Hz, 1H), 7.53-7.14 (m, 9H), 5.00 (s, 2H), 4.42 (d, J=6.0 Hz, 2H); 3.88 (td, J=7.2, 6.3 Hz, 3H), 1.15 (t, J=7.2 Hz, 3H); $^{13}$C NMR (150 MHz, DMSO-d$_6$): δ 167.7, 161.9 (d, $J_{CF}$=241.5 Hz), 160.6, 155.1, 146.8, 135.9 (d, $J_{CF}$=3.5 Hz), 134.5, 129.33, 129.29 (d, $J_{CF}$=9.2 Hz), 128.8, 128.3, 115.1 (d, $J_{CF}$=21.9 Hz), 79.0, 77.4, 41.0, 36.2, 14.4.

N-(2,5-Difluorobenzyl)-1-(benzyloxy)-4-(ethylamino)-1,2,3,6-tetrahydro-2,6-dioxopyrimidine-5-carboxamide (6-xvii)

White solid, 72% yield; $^1$H NMR (600 MHz, DMSO-d$_6$): δ 11.25 (s, 1H), 11.04 (t, J=5.4 Hz, 1H), 9.88 (t, J=6.0 Hz, 1H), 7.54-7.11 (m, 8H), 5.02 (s, 2H), 4.47 (d, J=6.0 Hz, 2H), 3.38 (td, J=7.2, 6.6 Hz, 2H), 1.15 (t, J=7.2 Hz, 3H).

N-(2,4-Difluorobenzyl)-1-(benzyloxy)-4-(ethylamino)-1,2,3,6-tetrahydro-2,6-dioxopyrimidine-5-carboxamide (6-xviii)

White solid, 61% yield; $^1$H NMR (600 MHz, DMSO-d$_6$): δ 11.25 (s, 1H), 11.08 (t, J=6.0 Hz, 1H), 9.85 (t, J=6.0 Hz, 1H), 7.54-7.05 (m, 8H), 5.01 (s, 2H), 4.45 (d, J=5.4 Hz, 2H); 3.37 (td, J=7.2, 6.6 Hz, 2H), 1.13 (t, J=7.2 Hz, 3H).

N-(3,5-Difluorobenzyl)-1-(benzyloxy)-4-(ethylamino)-1,2,3,6-tetrahydro-2,6-dioxopyrimidine-5-carboxamide (6-xix)

White solid, 73% yield; $^1$H NMR (600 MHz, DMSO-d$_6$): δ 11.26 (s, 1H), 11.06 (t, J=4.8 Hz, 1H), 9.92 (t, J=6.0 Hz, 1H), 7.50-6.89 (m, 8H), 4.99 (s, 2H), 4.43 (d, J=5.4 Hz, 2H); 3.35 (m, 2H), 1.15 (t, J=7.2 Hz, 3H).

N-(3,4-Difluorobenzyl)-1-(benzyloxy)-4-(ethylamino)-1,2,3,6-tetrahydro-2,6-dioxopyrimidine-5-carboxamide (6-xx)

White solid, 69% yield; $^1$H NMR (600 MHz, DMSO-d$_6$): δ 11.25 (s, 1H), 11.10 (t, J=5.4 Hz, 1H), 9.89 (t, J=6.0 Hz, 1H), 7.53-7.15 (m, 8H), 5.01 (s, 2H), 4.42 (d, J=6.6 Hz, 2H); 3.38 (td, J=7.2, 6.6 Hz, 2H), 1.15 (t, J=7.2 Hz, 3H).

N-(2-Chloro-5-fluorobenzyl)-1-(benzyloxy)-4-(ethylamino)-1,2,3,6-tetrahydro-2,6-dioxopyrimidine-5-carboxamide (6-xxi)

White solid, 83% yield; $^1$H NMR (600 MHz, DMSO-d$_6$): δ 11.26 (s, 1H), 11.02 (t, J=5.4 Hz, 1H), 9.94 (t, J=6.0 Hz, 1H), 7.55-7.10 (m, 8H), 5.03 (s, 2H), 4.49 (d, J=6.0 Hz, 2H), 3.38 (td, J=7.2, 6.6 Hz, 2H), 1.13 (t, J=7.2 Hz, 3H); $^{13}$C NMR (150 MHz, DMSO-d$_6$): δ 168.0, 160.9 (d, $J_{CF}$=242.7 Hz), 160.6, 155.1, 146.9, 139.4 (d, $J_{CF}$=6.9 Hz), 134.5, 130.9 (d, $J_{CF}$=9.2 Hz), 129.3, 128.8, 128.3, 127.1 (d, $J_{CF}$=3.5 Hz), 115.5 (d, $J_{CF}$=23 Hz), 115.4 (d, $J_{CF}$=23 Hz), 79.0, 77.5, 39.9, 36.2, 14.4.

N-(4-Chloro-3-fluorobenzyl)-1-(benzyloxy)-4-(ethylamino)-1,2,3,6-tetrahydro-2,6-dioxopyrimidine-5-carboxamide (6-xxii)

White solid, 59% yield; $^1$H NMR (600 MHz, DMSO-d$_6$): δ 11.25 (s, 1H), 11.08 (t, J=5.4 Hz, 1H), 9.91 (t, J=6.0 Hz, 1H), 7.55-7.15 (m, 8H), 5.01 (s, 2H), 4.44 (d, J=6.0 Hz, 2H), 3.38 (td, J=7.2, 6.6 Hz, 2H), 1.15 (t, J=7.2 Hz, 3H); $^{13}$C NMR (150 MHz, DMSO-d$_6$): δ 167.9, 160.6, 157.0 (d, $J_{CF}$=245 Hz), 155.1, 146.8, 142.0 (d, $J_{CF}$=6.9 Hz), 134.5, 130.4, 129.3, 128.8, 128.3, 124.4 (d, $J_{CF}$=3.5 Hz), 117.5 (d, $J_{CF}$=18.5 Hz), 115.5 (d, $J_{CF}$=20.7 Hz), 79.0, 77.5, 40.9, 36.2, 14.4.

N-(3-Chloro-2-fluorobenzyl)-1-(benzyloxy)-4-(ethylamino)-1,2,3,6-tetrahydro-2,6-dioxopyrimidine-5-carboxamide (6-xxiii)

White solid, 67% yield; $^1$H NMR (600 MHz, DMSO-d$_6$): δ 11.25 (s, 1H), 11.05 (t, J=5.4 Hz, 1H), 9.90 (t, J=6.0 Hz, 1H), 7.54-7.19 (m, 8H), 5.01 (s, 2H), 4.52 (d, J=5.4 Hz, 2H), 3.38 (td, J=7.2, 6.6 Hz, 2H), 1.14 (t, J=7.2 Hz, 3H).

N-(3-Fluoro-4-methylbenzyl)-1-(benzyloxy)-4-(ethylamino)-1,2,3,6-tetrahydro-2,6-dioxopyrimidine-5-carboxamide (6-xxiv)

White solid, 79% yield; $^1$H NMR (600 MHz, DMSO-d$_6$): δ 11.24 (s, 1H), 11.14 (t, J=5.4 Hz, 1H), 9.85 (t, J=5.4 Hz, 1H), 7.53-7.02 (m, 8H), 5.00 (s, 2H), 4.40 (d, J=5.4 Hz, 2H), 3.38 (td, J=7.2, 6.0 Hz, 2H), 2.20 (s, 3H), 1.15 (dd, J=7.2, 6.6 Hz, 3H); $^{13}$C NMR (150 MHz, DMSO-d$_6$): δ 167.8, 160.6 160.5 (d, $J_{CF}$=241.5 Hz), 155.1, 146.8, 139.9 (d, $J_{CF}$=6.9 Hz), 134.5, 131.5 (d, $J_{CF}$=5.7 Hz), 129.3, 128.7, 128.3, 123.0 (d, $J_{CF}$=3.5 Hz), 122.4 (d, $J_{CF}$=16.1 Hz), 113.7 (d, $J_{CF}$=21.9 Hz), 79.0, 77.4, 41.1, 36.2, 14.4, 13.8 (d, $J_{CF}$=3.5 Hz).

1-(Benzyloxy)-4-(ethylamino)-1,2,3,6-tetrahydro-2,6-dioxo-N-phenylpyrimidine-5-carboxamide (6-xxv)

White solid, 75% yield; $^1$H NMR (600 MHz, DMSO-d$_6$): δ 11.76 (s, 1H), 11.39 (s, 1H), 11.02 (t, J=6.0 Hz, 1H), 7.59-7.05 (m, 10H), 5.06 (s, 2H), 3.39 (qd, J=6.6, 6.0 Hz, 2H), 1.16 (t, J=6.6 Hz, 3H); $^{13}$C NMR (150 MHz, DMSO-$d_6$): δ 166.3, 161.2, 155.3, 146.7, 138.4, 134.5, 129.4, 128.9, 128.8, 128.4, 123.3, 119.9, 79.5, 77.6, 36.4, 14.4.

1-(Benzyloxy)-4-(ethylamino)-1,2,3,6-tetrahydro-2,6-dioxo-N-phenethylpyrimidine-5-carboxamide (6-xxvi)

White solid, 71% yield; $^1$H NMR (600 MHz, DMSO-$d_6$): δ 11.24 (s, 1H), 11.20 (s, 1H), 9.53 (s, 1H), 7.53-7.20 (m, 10H), 4.99 (s, 2H), 3.45 (td, J=6.6, 6.0 Hz, 2H), 3.37 (qd, J=7.2, 6.0 Hz, 2H), 2.79 (t, J=6.6 Hz, 2H), 1.16 (t, J=7.2 Hz, 3H); $^{13}$C NMR (150 MHz, DMSO-$d_6$): δ 167.7, 160.5, 155.0, 146.9, 139.4, 134.5, 129.4, 128.8, 128.6, 128.34, 128.31, 126.1, 79.0, 77.5, 41.8, 36.1, 35.4, 14.4.

1-(Benzyloxy)-N-(2-chloromethyl)-4-(ethylamino)-1,2,3,6-tetrahydro-2,6-dioxopyrimidine-5-carboxamide (6-xxvii)

White solid, 64% yield; $^1$H NMR (600 MHz, DMSO-$d_6$): δ 11.25 (s, 1H), 11.12 (t, J=5.4 Hz, 1H), 9.70 (t, J=6.0 Hz, 1H), 7.54-7.39 (m, 5H), 5.01 (s, 2H), 3.70 (dd, J=6.6, 6.0 Hz, 2H), 3.57 (ddd, J=6.6, 6.0, 5.4 Hz, 2H), 3.39 (td, J=7.2, 6.6 Hz, 2H), 1.16 (t, J=7.2 Hz, 3H); $^{13}$C NMR (150 MHz, DMSO-$d_6$): δ 168.1, 160.6, 155.1, 146.9, 134.5, 129.4, 128.8, 128.4, 79.0, 77.5, 43.8, 40.2, 36.2, 14.4.

N-(3-Chloro-2-fluorobenzyl)-1-(benzyloxy)-1,2,3,6-tetrahydro-2,6-dioxo-4-(propylamino)pyrimidine-5-carboxamide (6-xxviii)

White solid, 68% yield; $^1$H NMR (600 MHz, DMSO-$d_6$): δ 11.28 (s, 1H), 11.16 (dd, J=6.0, 4.8 Hz, 1H), 9.91 (t, J=6.0 Hz, 1H), 7.54-7.19 (m, 8H), 5.01 (s, 2H) 4.52 (d, J=6.0 Hz, 2H), 3.32 (m, 2H), 1.53 (m, 2H), 0.90 (dd, J=7.8, 7.2 Hz, 3H); $^{13}$C NMR (150 MHz, DMSO-$d_6$): δ 167.9, 160.6, 155.25, 155.18 (d, $J_{CF}$=246 Hz), 146.8, 134.5, 129.3, 129.1, 128.8, 128.5 (d, $J_{CF}$=14.9 Hz), 128.30, 128.28 (d, $J_{CF}$=5.7 Hz), 125.3 (d, $J_{CF}$=4.5 Hz), 119.4 (d, $J_{CF}$=17.3 Hz), 79.0, 77.5, 42.7, 35.9 (d, $J_{CF}$=4.5 Hz), 22.0, 11.0.

N-Benzyl-1-(hydroxy)-1,2,3,6-tetrahydro-2,6-dioxo-4-(phenylamino)pyrimidine-5-carboxamide (7-i)

White solid, 50% yield; $^1$H NMR (600 MHz, DMSO-$d_6$): δ 12.72 (s, 1H), 11.26 (s, 1H), 10.32 (s, 1H), 10.03 (t, J=2.4, 1H), 7.43-7.26 (m, 10H), 4.49 (s, 2H); $^{13}$C NMR (150 MHz, DMSO-$d_6$): δ 167.7, 161.6, 154.0, 147.0, 139.3, 135.8, 129.5, 128.4, 127.2, 126.9, 126.5, 124.9, 81.7, 41.9; HRMS-ESI(−) m/z calcd for $C_{18}H_{16}N_4O_4$ 351.1099 [M-H]$^-$, found 351.1118.

N-Benzyl-1-(hydroxy)-1,2,3,6-tetrahydro-2,6-dioxo-4-(biphenylamino)pyrimidine-5-carboxamide (7-ii)

White solid, 77% yield; $^1$H NMR (600 MHz, DMSO-$d_6$): δ 12.76 (s, 1H), 11.33 (s, 1H), 10.34 (s, 1H), 10.04 (dd, J=6.0, 4.8 1H), 7.74-7.20 (m, 14H), 4.50 (d, J=5.4 Hz, 2H); $^{13}$C NMR (150 MHz, DMSO-$d_6$): δ 167.7, 161.6, 154.0, 147.0, 139.3, 138.1, 135.2, 129.0, 128.4, 127.7, 127.5, 127.2, 126.9, 126.5, 125.4, 80.9, 41.9.

N-(3-Fluorobenzyl)-1-(hydroxy)-1,2,3,6-tetrahydro-2,6-dioxo-4-(biphenylamino)pyrimidine-5-carboxamide (7-iii)

White solid, 21% yield; $^1$H NMR (600 MHz, DMSO-$d_6$): δ 12.69 (s, 1H), 11.34 (s, 1H), 10.34 (s, 1H), 10.08 (t, J=6.0, 1 H), 7.74-7.07 (m, 13H), 4.52 (d, J=6.0, 2H); $^{13}$C NMR (150 MHz, DMSO-$d_6$): δ 167.8, 162.2 (d, $J_{CF}$=241.8 Hz), 161.6, 154.0, 147.0, 142.6 (d, $J_{CF}$=6.6 Hz), 139.3, 138.1, 135.2, 130.3 (d, $J_{CF}$=7.7 Hz), 129.0, 127.7, 127.5, 126.9, 126.5, 125.4, 123.2 (d, $J_{CF}$=3.6 Hz), 113.8 (d, $J_{CF}$=21.8 Hz), 113.6 (d, $J_{CF}$=20.7 Hz), 80.9, 41.4.

N-(4-Fluorobenzyl)-1-(hydroxy)-1,2,3,6-tetrahydro-2,6-dioxo-4-(biphenylamino)pyrimidine-5-carboxamide (7-iv)

White solid, 19% yield; $^1$H NMR (600 MHz, DMSO-$d_6$): δ 12.73 (s, 1H), 11.32 (s, 1H), 10.33 (s, 1H), 10.04 (t, J=6.0, 1H), 7.74-7.15 (m, 13H), 4.48 (d, J=6.0, 2H); $^{13}$C NMR (150 MHz, DMSO-$d_6$): δ 167.8, 161.6, 161.2 (d, $J_{CF}$=240.8 Hz), 154.0, 147.0, 139.3, 138.1, 135.6 (d, $J_{CF}$=3.2 Hz), 135.2, 129.2 (d, $J_{CF}$=7.7 Hz), 129.0, 127.7, 127.5, 126.5, 125.4, 115.1 (d, $J_{CF}$=20.6 Hz), 80.9, 41.1.

N-Benzyl-1-(hydroxy)-1,2,3,6-tetrahydro-4-(methylamino)-2,6 dioxopyrimidine-5-carboxamide (7-v)

White solid, 39% yield; $^1$H NMR (600 MHz, DMSO-$d_6$): δ 11.05 (s, 1H), 10.88 (q, J=4.8 Hz, 1H), 10.20 (s, 1H), 9.90 (t, J=6.0 Hz, 1H), 7.33-7.22 (m, 5H), 4.43 (d, J=6.0 Hz, 2H); 2.94 (d, J=5.4 Hz, 3H); $^{13}$C NMR (150 MHz, DMSO-$d_6$): δ 167.7, 161.3, 155.7, 147.3, 139.7, 128.3, 127.1, 126.7, 79.0, 41.7, 28.4

N-Benzyl-1-(hydroxy)-4-(ethylamino)-1,2,3,6-tetrahydro-2,6-dioxopyrimidine-5-carboxamide (7-vi)

White solid, 42% yield; $^1$H NMR (600 MHz, DMSO-$d_6$): δ 11.11 (s, 1H), 11.04 (t, J=5.4 Hz, 1H), 10.20 (s, 1H), 9.93 (t, J=6.0 Hz, 1H), 7.34-7.24 (m, 5H), 4.43 (d, J=6.0 Hz, 2H); 3.36 (td, J=6.6, 6.0 Hz, 2H), 1.14 (t, J=6.6 Hz, 3H); $^{13}$C NMR (150 MHz, DMSO-$d_6$): δ 167.8, 161.4, 154.7, 147.3, 139.6, 128.4, 127.1, 126.8, 78.8, 41.7, 36.0, 14.4.

N-Benzyl-1-(hydroxy)-1,2,3,6-tetrahydro-2,6-dioxo-4-(propylamino)pyrimidine-5-carboxamide (7-vii)

White solid, 79% yield; $^1$H NMR (600 MHz, DMSO-$d_6$): δ 11.16 (s, 1H), 11.13 (s, 1H), 10.20 (s, 1H), 9.94 (s, 1H), 7.32-7.24 (m, 5H), 4.44 (d, J=4.8 Hz, 2H); 3.30 (m, 2H), 1.54 (m, 2H), 0.91 (t, J=6.6 Hz, 3H); $^{13}$C NMR (150 MHz, DMSO-$d_6$): δ 167.9, 161.4, 154.9, 147.3, 139.6, 128.4, 127.1, 126.8, 78.8, 42.6, 41.7, 22.1, 11.0.

N-Benzyl-1-(hydroxy)-1,2,3,6-tetrahydro-4-(isopropylamino)-2,6-dioxopyrimidine-5-carboxamide (7-viii)

White solid, 92% yield; $^1$H NMR (600 MHz, DMSO-$d_6$): δ 11.18 (d, J=8.4 Hz 1H), 11.14 (s, 1H), 10.21 (s, 1H), 9.96 (d, J=5.4 Hz 1H), 7.34-7.23 (m, 5H), 4.43 (d, J=5.4 Hz, 2H); 4.08 (m, 1H), 1.16 (d, J=6.0 Hz, 6H); $^{13}$C NMR (150 MHz, DMSO-$d_6$): δ 167.9, 161.4, 153.8, 147.3, 139.6, 128.4, 127.1, 126.8, 78.7, 42.6, 41.7, 22.8.

N-Benzyl-1-(hydroxy)-4-(cyclopropylamino)-1,2,3,6-tetrahydro-2,6-dioxopyrimidine-5-carboxamide (7-ix)

White solid, 82% yield; $^1$H NMR (600 MHz, DMSO-$d_6$): δ 11.17 (s, 1H), 11.01 (s, 1H), 10.24 (s, 1H), 9.87 (t, J=6.0 Hz 1H), 7.31-7.21 (m, 5H), 4.39 (d, J=5.4 Hz, 2H); 2.71 (m, 1H), 0.83 (m, 2H), 0.59 (m, 2H); $^{13}$C NMR (150 MHz, DMSO-d$_6$): δ 167.6, 161.2, 156.5, 147.1, 139.5, 128.4, 127.1, 126.8, 79.2, 41.7, 23.0, 7.7.

4-(tert-Butylamino)-N-benzyl-1-(hydroxy)-1,2,3,6-tetrahydro-2,6-dioxopyrimidine-5-carboxamide (7-x)

White solid, 59% yield; $^1$H NMR (600 MHz, DMSO-d$_6$): δ 11.82 (s, 1H), 10.24 (s, 1H), 10.10 (t, J=6.0 Hz, 1H), 10.03 (brs, 1H), 7.33-7.25 (m, 5H), 4.43 (d, J=5.4 Hz, 2H), 1.41 (s, 9H); $^{13}$C NMR (150 MHz, DMSO-d$_6$): δ 168.1, 161.4, 153.7, 146.8, 139.5, 128.4, 127.1, 126.8, 78.9, 52.0, 41.7, 29.0.

4-Amino-N-benzyl-1-(hydroxy)-1,2,3,6-tetrahydro-2,6-dioxopyrimidine-5-carboxamide (7-xi)

White solid, 89% yield; $^1$H NMR (600 MHz, DMSO-d$_6$): δ 11.19 (brs, 1H), 10.13 (brs, 1H), 9.78 (s, 1H), 9.68 (s, 1H), 7.32-7.24 (m, 4H), 6.88 (brs, 1H), 4.43 (d, J=4.8 Hz, 2H); $^{13}$C NMR (150 MHz, DMSO-d$_6$): δ 167.1, 161.8, 156.4, 147.5, 139.7, 128.3, 127.1, 126.7, 79.8, 41.6.

N-(3-Fluorobenzyl)-1-(hydroxy)-1,2,3,6-tetrahydro-4-(methylamino)-2,6-dioxopyrimidine-5-carboxamide (7-xii)

White solid, 20% yield; $^1$H NMR (600 MHz, DMSO-d$_6$): δ 11.05 (s, 1H), 10.80 (q, J=4.8 Hz, 1H), 10.18 (s, 1H), 9.94 (t, J=6.0 Hz, 1H), 7.35 (ddd, J=7.8, 7.2, 6.0 Hz, 1H), 7.11 (d, J=7.2 Hz, 1H), 7.06 (m, 2H), 4.44 (d, J=6.0 Hz, 2H); 2.93 (d, J=4.2 Hz, 3H); $^{13}$C NMR (150 MHz, DMSO-d$_6$): δ 167.8, 162.2 (d, J$_{CF}$=241.5 Hz), 161.3, 155.9, 147.4, 143.0 (d, J$_{CF}$=6.9 Hz), 130.2 (d, J$_{CF}$=8.1 Hz), 123.1 (d, J$_{CF}$=2.4 Hz), 113.7 (d, J$_{CF}$=21.9 Hz), 113.4 (d, J$_{CF}$=20.0 Hz), 79.0, 41.2, 28.4.

N-(4-Fluorobenzyl)-1-(hydroxy)-1,2,3,6-tetrahydro-4-(methylamino)-2,6-dioxopyrimidine-5-carboxamide (7-xiii)

White solid, 20% yield; $^1$H NMR (600 MHz, DMSO-d$_6$): δ 11.05 (s, 1H), 10.86 (q, J=5.4 Hz, 1H), 10.19 (s, 1H), 9.87 (t, J=6.0 Hz, 1H), 7.31 (dd, J=8.4, 5.4 Hz, 2H), 7.14 (t, J=9.0 Hz, 2H), 4.41 (d, J=5.4 Hz, 2H); 2.94 (d, J=4.8 Hz, 3H); $^{13}$C NMR (150 MHz, DMSO-d$_6$): δ 167.7, 163.7, 161.1 (d, J$_{CF}$=241.5 Hz), 161.2, 155.7, 147.3, 136.0 (d, J$_{CF}$=2.4 Hz), 129.1 (d, J$_{CF}$=8.1 Hz), 115.0 (d, J$_{CF}$=20.7 Hz), 79.0, 40.9, 28.4.

N-(3-Chloro-2-fluorobenzyl)-1-(hydroxy)-1,2,3,6-tetrahydro-4-(methylamino)-2,6-dioxopyrimidine-5-carboxamide (7-xiv)

White solid, 90% yield; $^1$H NMR (600 MHz, DMSO-d$_6$): δ 11.06 (s, 1H), 10.76 (q, J=4.2 Hz, 1H), 10.22 (s, 1H), 9.95 (t, J=6.0 Hz, 1H), 7.47 (t, J=7.2 Hz, 1H), 7.27 (dd, J=7.8, 6.0 Hz, 1H), 7.18 (t, J=7.8 Hz, 1H), 4.50 (d, J=4.8 Hz, 2H), 2.93 (d, J=4.2 Hz, 3H); $^{13}$C NMR (150 MHz, DMSO-d$_6$): δ 167.8, 161.3, 155.7, 155.2 (d, J$_{CF}$=246 Hz), 147.3, 129.0, 128.7 (d, J$_{CF}$=13.8 Hz), 128.2 (d, J$_{CF}$=4.5 Hz), 125.2 (d, J$_{CF}$=4.7 Hz), 119.4 (d, J$_{CF}$=17.3 Hz), 79.0, 35.9 (d, J$_{CF}$=3.5 Hz), 28.4.

N-(3-Fluorobenzyl)-1-(hydroxy)-4-(ethylamino)-1,2,3,6-tetrahydro-2,6-dioxopyrimidine-5-carboxamide (7-xv)

White solid, 76% yield; $^1$H NMR (600 MHz, DMSO-d$_6$): δ 11.11 (s, 1H), 11.98 (t, J=4.8 Hz, 1H), 10.22 (s, 1H), 9.97 (t, J=6.0 Hz, 1H), 7.36 (q, 7.2 Hz, 1H), 7.11 (d, J=7.2 Hz, 1H), 7.06 (m, 2H), 4.45 (d, J=6.0 Hz, 2H); 3.36 (td, J=7.2, 6.6 Hz, 2H), 1.14 (t, J=7.2 Hz, 3H); $^{13}$C NMR (150 MHz, DMSO-d$_6$): δ 167.9, 161.5 (d, J$_{CF}$=241.5 Hz), 161.4, 154.7, 147.3, 142.9 (d, J$_{CF}$=6.9 Hz), 130.3 (d, J$_{CF}$=8.0 Hz), 123.0, 113.7 (d, J$_{CF}$=21.8 Hz), 113.5 (d, J$_{CF}$=20.7 Hz), 78.8, 41.2, 36.1, 14.4.

N-(4-Fluorobenzyl)-1-(hydroxy)-4-(ethylamino)-1,2,3,6-tetrahydro-2,6-dioxopyrimidine-5-carboxamide (7-xvi)

White solid, 33% yield; $^1$H NMR (600 MHz, DMSO-d$_6$): δ 11.10 (s, 1H), 11.01 (t, J=5.4 Hz, 1H), 10.20 (s, 1H), 9.93 (t, J=6.0 Hz, 1H), 7.31 (dd, J=8.4, 5.4 Hz, 2H), 7.14 (t, J=9.0 Hz, 2H), 4.41 (d, J=5.4 Hz, 2H); 3.36 (td, J=7.2, 6.6 Hz, 3H), 1.14 (t, J=7.2 Hz, 3H); $^{13}$C NMR (150 MHz, DMSO-d$_6$): δ 167.8, 161.3, 161.1 (d, J$_{CF}$=240.3 Hz), 154.7, 147.3, 135.9 (d, J$_{CF}$=2.3 Hz), 129.1 (d, J$_{CF}$=8.0 Hz), 115.0 (d, J$_{CF}$=21.9 Hz), 78.8, 40.9, 36.0, 14.4.

N-(2,5-Difluorobenzyl)-1-(hydroxy)-4-(ethylamino)-1,2,3,6-tetrahydro-2,6-dioxopyrimidine-5-carboxamide (7-xvii)

White solid, 32% yield; $^1$H NMR (600 MHz, DMSO-d$_6$): δ 11.12 (s, 1H), 11.90 (t, J=5.4 Hz, 1H), 10.23 (s, 1H), 9.96 (t, J=6.0 Hz, 1H), 7.25-7.07 (m, 3H), 4.45 (d, J=5.4 Hz, 2H); 3.36 (td, J=7.2, 6.6 Hz, 2H), 1.13 (t, J=7.2 Hz, 3H).

N-(2,4-Difluorobenzyl)-1-(hydroxy)-4-(ethylamino)-1,2,3,6-tetrahydro-2,6-dioxopyrimidine-5-carboxamide (7-xviii)

White solid, 26% yield; $^1$H NMR (600 MHz, DMSO-d$_6$): δ 11.11 (s, 1H), 10.91 (t, J=5.4 Hz, 1H), 10.19 (s, 1H), 9.94 (t, J=6.0 Hz, 1H), 7.36-7.04 (m, 3H), 4.43 (d, J=6.0 Hz, 2H); 3.35 (td, J=7.2, 6.6 Hz, 2H), 1.13 (t, J=7.2 Hz, 3H).

N-(3,5-Difluorobenzyl)-1-(hydroxy)-4-(ethylamino)-1,2,3,6-tetrahydro-2,6-dioxopyrimidine-5-carboxamide (7-xix)

White solid, 61% yield; $^1$H NMR (600 MHz, DMSO-d$_6$): δ 11.12 (s, 1H), 10.92 (t, J=4.8 Hz, 1H), 10.23 (s, 1H), 9.99 (t, J=6.0 Hz, 1H), 7.08-6.96 (m, 3H), 4.45 (d, J=6.0 Hz, 2H); 3.36 (td, J=7.2, 6.6 Hz, 2H), 1.14 (t, J=7.2 Hz, 3H).

N-(3,4-Difluorobenzyl)-1-(hydroxy)-4-(ethylamino)-1,2,3,6-tetrahydro-2,6-dioxopyrimidine-5-carboxamide (7-xx)

White solid, 56% yield; $^1$H NMR (600 MHz, DMSO-d$_6$): δ 11.11 (s, 1H), 10.96 (s, 1H), 10.21 (s, 1H), 9.96 (s, 1H), 7.38-7.16 (m, 3H), 4.41 (d, J=3.6 Hz, 2H); 3.36 (m, 2H), 1.14 (dd, J=7.2, 4.8 Hz, 3H).

N-(2-Chloro-5-fluorobenzyl)-1-(hydroxy)-4-(ethylamino)-1,2,3,6-tetrahydro-2,6-dioxopyrimidine-5-carboxamide (7-xxi)

White solid, 20% yield; $^1$H NMR (600 MHz, DMSO-d$_6$): δ 11.13 (s, 1H), 10.88 (dd, J=5.4, 4.2 Hz, 1H), 10.24 (s, 1H), 10.03 (t, J=6.0 Hz, 1H), 7.50 (dd, J=9.0, 5.4 Hz, 1H), 7.16 (td, J=8.4, 3.0 Hz, 1H), 7.09 (dd, J=9.6, 2.4 Hz, 1H), 4.47 (d, J=6.0 Hz, 2H), 3.35 (td, J=7.2, 6.6 Hz, 2H), 1.13 (t, J=7.2 Hz, 3H); $^{13}$C NMR (150 MHz, DMSO-d$_6$): δ 168.0, 161.4, 160.8 (d, $J_{CF}$=242.7 Hz), 154.7, 147.3, 139.5 (d, $J_{CF}$=6.9 Hz), 130.9 (d, $J_{CF}$=8.1 Hz), 127.2 (d, $J_{CF}$=2.3 Hz), 116.2 (d, $J_{CF}$=24.2 Hz), 115.4 (d, $J_{CF}$=23.1 Hz), 78.8, 39.8, 36.1, 14.3.

N-(4-Chloro-3-fluorobenzyl)-1-(hydroxy)-4-(ethylamino)-1,2,3,6-tetrahydro-2,6-dioxopyrimidine-5-carboxamide (7-xxii)

White solid, 51% yield; $^1$H NMR (600 MHz, DMSO-d$_6$): δ 11.12 (s, 1H), 10.94 (t, J=5.4 Hz, 1H), 10.22 (s, 1H), 9.98 (t, J=6.0 Hz, 1H), 7.53 (dd, J=8.4, 7.2 Hz, 1H), 7.28 (d, J=10.8 Hz, 1H), 7.19 (d, J=8.4 Hz, 1H), 4.43 (d, J=6.0 Hz, 2H), 3.36 (td, J=7.2, 6.6 Hz, 2H), 1.13 (t, J=7.2 Hz, 3H); $^{13}$C NMR (150 MHz, DMSO-d$_6$): δ 168.0, 161.3, 157.0 (d, $J_{CF}$=244.8 Hz), 154.7, 147.3, 142.0 (d, $J_{CF}$=5.7 Hz), 130.4, 124.2 (d, $J_{CF}$=3.4 Hz), 117.4 (d, $J_{CF}$=17.3 Hz), 115.4 (d, $J_{CF}$=20.7 Hz), 78.8, 40.8, 36.1, 14.3.

N-(3-Chloro-2-fluorobenzyl)-1-(hydroxy)-4-(ethylamino)-1,2,3,6-tetrahydro-2,6-dioxopyrimidine-5-carboxamide (7-xxiii)

White solid, 90% yield; $^1$H NMR (600 MHz, DMSO-d$_6$): δ 11.12 (s, 1H), 10.90 (t, J=5.4 Hz, 1H), 10.23 (s, 1H), 9.99 (t, J=6.0 Hz, 1H), 7.48 (t, J=7.2 Hz, 1H), 7.27 (dd, J=7.2 Hz, 1H), 7.19 (t, J=7.8 Hz, 1H), 4.50 (d, J=4.2 Hz, 2H), 3.35 (td, J=7.2, 6.6 Hz, 2H), 1.13 (t, J=7.2 Hz, 3H); $^{13}$C NMR (150 MHz, DMSO-d$_6$): δ 167.9, 161.4, 155.2 (d, $J_{CF}$=244.8 Hz), 154.7, 147.3, 129.1, 128.6 (d, $J_{CF}$=13.8 Hz), 128.2 (d, $J_{CF}$=3.5 Hz), 125.2 (d, $J_{CF}$=4.5 Hz), 119.4 (d, $J_{CF}$=17.3 Hz), 78.8, 36.0, 35.9 (d, $J_{CF}$=3.5 Hz), 14.4.

N-(3-Fluoro-4-methylbenzyl)-1-(hydroxy)-4-(ethylamino)-1,2,3,6-tetrahydro-2,6-dioxopyrimidine-5-carboxamide (7-xxiv)

White solid, 37% yield; $^1$H NMR (600 MHz, DMSO-d$_6$): δ 11.11 (s, 1H), 11.00 (t, J=5.4 Hz, 1H), 10.21 (s, 1H), 9.93 (t, J=5.4 Hz, 1H), 7.22 (t, J=7.8 Hz, 1H), 7.01 (m, 2H), 4.39 (d, J=6.0 Hz, 2H), 3.36 (td, J=6.6, 6.0 Hz, 2H), 2.19 (s, 3H), 1.13 (dd, J=7.2, 6.6 Hz, 3H); $^{13}$C NMR (150 MHz, DMSO-d$_6$): δ 167.9, 161.4, 160.5 (d, $J_{CF}$=239.3 Hz), 154.7, 147.3, 139.9 (d, $J_{CF}$=6.9 Hz), 131.5 (d, $J_{CF}$=5.7 Hz), 122.8 (d, $J_{CF}$=3.5 Hz), 122.3 (d, $J_{CF}$=17.3 Hz), 113.5 (d, $J_{CF}$=21.8 Hz), 78.8, 41.0, 36.0, 14.4, 13.8 (d, $J_{CF}$=3.5 Hz).

1-(Hydroxy)-4-(ethylamino)-1,2,3,6-tetrahydro-2,6-dioxo-N-phenylpyrimidine-5-carboxamide (7-xxv)

White solid, 83% yield; $^1$H NMR (600 MHz, DMSO-d$_6$): δ 11.89 (s, 1H), 11.26 (s, 1H), 10.89 (t, J=5.4 Hz, 1H), 10.38 (s, 1H), 7.55 (d, J=7.8 Hz, 2H), 7.31 (dd, J=7.8, 7.2 Hz, 2H), 7.31 (dd, J=7.8, 7.2 Hz, 1H), 3.42 (qd, J=6.6, 6.0 Hz, 2H), 1.18 (t, J=6.6 Hz, 3H); $^{13}$C NMR (150 MHz, DMSO-d$_6$): δ 166.3, 161.8, 154.9, 147.1, 138.5, 128.9, 123.1, 119.8, 79.2, 36.3, 14.4.

1-(Hydroxy)-4-(ethylamino)-1,2,3,6-tetrahydro-2,6-dioxo-N-phenethylpyrimidine-5-carboxamide (7-xxvi)

White solid, 79% yield; $^1$H NMR (600 MHz, DMSO-d$_6$): δ 11.11 (t, J=5.4 Hz, 1H), 11.06 (s, 1H), 10.17 (s, 1H), 9.56 (t, J=5.4 Hz, 1H), 7.30-7.19 (m, 5H), 3.45 (ddd, J=7.2, 6.6, 6.0 Hz, 2H); 3.35 (qd, J=7.2, 6.6 Hz, 2H), 2.77 (t, J=7.2 Hz, 3H), 1.14 (t, J=7.2 Hz, 3H); $^{13}$C NMR (150 MHz, DMSO-d$_6$): δ 167.8, 161.2, 154.6, 147.3, 139.4, 128.6, 128.4, 126.1, 78.9, 41.7, 36.0, 35.3, 14.4.

1-(Hydroxy)-N-(2-chloroethyl)-4-(ethylamino)-1,2,3,6-tetrahydro-2,6-dioxopyrimidine-5-carboxamide (7-xxvii)

White solid, 83% yield; $^1$H NMR (600 MHz, DMSO-d$_6$): δ 11.11 (s, 1H), 11.98 (s, 1H), 10.22 (s, 1H), 9.78 (s, 1H), 3.68 (m, 2H), 3.55 (m, 2H), 3.37 (m, 2H), 1.15 (t, J=6.6 Hz, 3H); $^{13}$C NMR (150 MHz, DMSO-d$_6$): δ 168.0, 161.2, 154.7, 147.3, 78.7, 43.97, 40.1, 36.1, 14.4.

N-(3-Chloro-2-fluorobenzyl)-1-(hydroxy)-1,2,3,6-tetrahydro-2,6-dioxo-4-(propylamino)pyrimidine-5-carboxamide (7-xxvii)

White solid, 73% yield; $^1$H NMR (600 MHz, DMSO-d$_6$): δ 11.15 (s, 1H), 11.02 (s, 1H), 10.23 (s, 1H), 9.99 (s, 1H), 7.47-7.18 (m, 3H), 4.51 (d, J=4.2 Hz, 2H), 3.30 (m, 2H), 1.52 (m, 2H), 0.89 (dd, J=7.8, 6.0 Hz, 3H); $^{13}$C NMR (150 MHz, DMSO-d$_6$): δ 168.0, 161.4, 155.2 (d, $J_{CF}$=246 Hz), 154.9, 147.3, 129.1, 128.6 (d, $J_{CF}$=14.9 Hz), 128.2 (d, $J_{CF}$=4.5 Hz), 125.3 (d, $J_{CF}$=3.5 Hz), 119.5 (d, $J_{CF}$=17.3 Hz), 78.8, 42.6, 35.9 (d, $J_{CF}$=3.5 Hz), 22.0, 11.0.

N-(2-Fluorobenzyl)-1-(hydroxy)-1,2,3,6-tetrahydro-2,6-dioxo-4-(biphenylamino)pyrimidine-5-carboxamide (7-xxix)

White solid, 48% yield; $^1$H NMR (600 MHz, DMSO-d$_6$): δ 12.67 (s, 1H), 11.35 (br s, 1H), 10.35 (s, 1H), 10.05 (dd, J=6.0, 5.4, 1H), 7.74-7.17 (m, 13H), 4.54 (d, J=5.4 Hz, 2H); $^{13}$C NMR (150 MHz, DMSO-d$_6$): δ 167.7, 161.6, 160.2 (d, $J_{CF}$=242.9 Hz), 154.0, 146.97, 139.3, 138.1, 135.1, 129.5 (d, $J_{CF}$=4.3 Hz), 129.0 (d, $J_{CF}$=10.8 Hz), 129.0, 127.7, 127.5, 126.5, 126.1 (d, $J_{CF}$=11.1 Hz), 125.4, 124.4 (d, $J_{CF}$=3.3 Hz), 115.2 (d, $J_{CF}$=20.6 Hz), 80.9, 36.0; HRMS-ESI(−) m/z calcd for C$_{24}$H$_{19}$FN$_4$O$_4$ 445.1318 [M-H]$^-$, found 445.1324.

N-(2,4-difluorobenzyl)-1-(hydroxy)-1,2,3,6-tetrahydro-2,6-dioxo-4-(biphenylamino) pyrimidine-5-carboxamide (7-xxx)

White solid, 55% yield; $^1$H NMR (600 MHz, DMSO-d6): δ 12.64 (s, 1H), 11.35 (s, 1H), 10.34 (s, 1H), 10.04 (s, 1H), 7.73-7.07 (m, 3H), 4.50 (d, J=5.4 Hz, 2H); HRMS-ESI(−) m/z calcd for C$_{24}$H$_{18}$F$_2$N$_4$O$_4$ 463.1223 [M-H]$^-$, found 463.1230.

N-(2,5-difluorobenzyl)-1-(hydroxy)-1,2,3,6-tetrahydro-2,6-dioxo-4-(biphenylamino) pyrimidine-5-carboxamide (7-xxxi)

White solid, 84% yield; $^1$H NMR (600 MHz, DMSO-d6): δ 12.59 (s, 1H), 11.35 (s, 1H), 10.35 (s, 1H), 10.07 (t, J=6.0 Hz, 1H), 7.73-7.15 (m, 3H), 4.53 (d, J=5.4 Hz, 2H); HRMS-ESI(−) m/z calcd for C$_{24}$H$_{18}$F$_2$N$_4$O$_4$ 463.1223 [M-H]$^-$, found 463.1227.

N-(3,5-difluorobenzyl)-1-(hydroxy)-1,2,3,6-tetrahydro-2,6-dioxo-4-(biphenylamino) pyrimidine-5-carboxamide (7-xxxii)

White solid, 25% yield; $^1$H NMR (600 MHz, DMSO-d6): δ 12.62 (s, 1H), 11.35 (br s, 1H), 10.35 (s, 1H), 10.09 (s, 1H), 7.73-7.02 (m, 3H), 4.52 (d, J=5.4 Hz, 2H); HRMS-ESI(−) m/z calcd for $C_{24}H_{18}F_2N_4O_4$ 463.1223 [M-H]−, found 463.1221.

N-(3-Chloro-2-fluorobenzyl)-1-(hydroxy)-1,2,3,6-tetrahydro-2,6-dioxo-4-(biphenylamino) pyrimidine-5-carboxamide (7-xxxiii)

White solid, 25% yield; $^1$H NMR (600 MHz, DMSO-d6): δ 12.60 (s, 1H), 11.37 (br s, 1H), 10.35 (s, 1H), 10.10 (dd, J=6.0, 5.4 Hz, 1H), 7.73-7.20 (m, 12H), 4.57 (d, J=6.0 Hz, 2H); $^{13}$C NMR (150 MHz, DMSO-d6): δ 167.8, 161.6, 155.2 (d, $J_{CF}$=246 Hz), 154.1, 147.0, 139.3, 138.1, 135.1, 129.2, 129.0, 128.4 (d, $J_{CF}$=10.4 Hz), 128.3 (d, $J_{CF}$=3.4 Hz), 127.7, 127.5, 126.5, 125.4, 125.3 (d, $J_{CF}$=4.5 Hz), 119.5 (d, $J_{CF}$=17.3 Hz), 80.9, 36.1 (d, $J_{CF}$=3.5 Hz); HRMS-ESI(−) m/z calcd for $C_{24}H_{18}ClFN_4O_4$ 479.0928 [M-H]−, found 479.0931.

1-(Hydroxy)-1,2,3,6-tetrahydro-2,6-dioxo-4-(phenylamino)pyrimidine-5-carboxamide (12)

White solid; $^1$H NMR (600 MHz, DMSO-d6): δ 12.90 (s, 1H), 11.20 (s, 1H), 10.27 (s, 1H), 8.96 (s, 1H), 7.44-7.27 (m, 5H); $^{13}$C NMR (150 MHz, DMSO-d6): δ 169.9, 161.4, 154.2, 147.0, 135.8, 129.6, 126.4, 124.9, 80.7; HRMS-ESI (−) m/z calcd for $C_{11}H_{10}N_4O_4$ 261.0629 [M-H]−, found 261.0632.

1-(Hydroxy)-4-(ethylamino)-1,2,3,6-tetrahydro-2,6-dioxo-N-phenylpyrimidine-5-carboxamide (13)

White solid, 83% yield; 1H NMR (600 MHz, DMSO-d6): δ 11.89 (s, 1H), 11.26 (s, 1H), 10.89 (t, J=5.4 Hz, 1H), 10.38 (s, 1H), 7.55 (d, J=7.8 Hz, 2H), 7.31 (dd, J=7.8, 7.2 Hz, 2H), 7.31 (dd, J=7.8, 7.2 Hz, 1H), 3.42 (qd, J=6.6, 6.0 Hz, 2H), 1.18 (t, J=6.6 Hz, 3H); 13C NMR (150 MHz, DMSO-d6): δ 166.3, 161.8, 154.9, 147.1, 138.5, 128.9, 123.1, 119.8, 79.2, 36.3, 14.4; HRMS-ESI(−) m/z calcd for $C_{13}H_{14}N_4O_4$ 289.0942 [M-H]−, found 289.0942.

Phenyl-1-(hydroxy)-4-(ethylamino)-1,2,3,6-tetrahydro-2,6-dioxopyrimidine-5-carboxylate (14)

White solid, 92% yield; $^1$H NMR (600 MHz, DMSO-d6): δ 11.16 (s, 1H), 10.12 (s, 1H), 9.49 (s, 1H), 7.41-7.09 (m, 5H), 3.42 (m, 2H), 1.14 (m, 3H); $^{13}$C NMR (150 MHz, DMSO-d6): δ 167.2, 157.2, 155.6, 150.7, 147.6, 129.3, 125.3, 122.1, 78.2, 36.5, 14.2; HRMS-ESI(−) m/z calcd for $C_{13}H_{13}N_3O_5$ 290.0782 [M-H]−, found 290.0784.

N-(4-Fluorobenzyl)-3-(hydroxy)-6-(ethylamino)-1,2,3,4-tetrahydro-1-methyl-2,4-dioxopyrimidine-5-carboxamide (7-xxxv)

White solid, 38% yield; $^1$H NMR (600 MHz, DMSO-d6): δ 11.89 (s, 1H), 10.29 (s, 1H), 9.93 (s, 1H), 7.32 (m, 2H), 7.14 (m, 2H), 4.43 (d, J=4.2 Hz, 2H), 4.00 (s, 3H), 3.47 (m, 2H), 1.16 (dd, J=6.6, 5.4 Hz, 3H); $^{13}$C NMR (150 MHz, DMSO-d6): δ 167.6, 161.1 (d, $J_{CF}$=240.3 Hz), 160.5, 159.8, 154.2, 135.9, 129.1 (d, $J_{CF}$=8.1 Hz), 115.0 (d, $J_{CF}$=20.7 Hz), 84.4, 55.6, 41.0, 35.2, 14.8; HRMS-ESI(−) m/z calcd for $C_{15}H_{17}FN_4O_4$ 335.1161 [M-H]−, found 335.1158.

3-(Benzyloxy)-6-(ethylamino)-N-(4-fluorobenzyl)-N-methyl-2,4-dioxo-1,2,3,4-tetrahydropyrimidine-5-carboxamide (15)

White solid, 28% yield; $^1$H NMR (600 MHz, DMSO-d6): δ 11.25 (s, 1H), 9.99 (s, 1H), 7.52-7.13 (m, 9H), 4.98 (s, 2H), 4.43 (s, 2H), 3.43 (m, 2H), 3.38 (s, 3H), 1.19 (dd, J=6.0, 5.4 Hz, 3H); $^{13}$C NMR (150 MHz, DMSO-d6): δ 167.5, 161.2 (d, $J_{CF}$=240.3 Hz), 161.0, 159.9, 148.5, 135.7, 134.4, 129.34, 129.31 (d, $J_{CF}$=8.1 Hz), 128.8, 128.3, 115.1 (d, $J_{CF}$=20.7 Hz), 83.4, 77.3, 41.6, 41.2, 35.9, 15.5; HRMS-ESI(−) m/z calcd for $C_{22}H_{23}FN_4O_4$ 425.1631 [M-H]−, found 425.1631. The INST $IC_{50}$ for this compound is 7.0±3.3 μM.

N-Benzyl-1,6-dihydroxy-2,4-dioxo-1,2,3,4-tetrahydropyrimidine-5-carboxamide (16)

Pale white solid, 53% yield; 1H NMR (600 MHz, DMSO-d6): δ 11.91 (s, 1H), 10.40 (s, 1H), 9.97 (s, 1H), 7.36-7.29 (m, 5H), 4.57 (brs, 2H); 13C NMR (150 MHz, DMSO-d6): δ 170.0, 147.6, 137.6, 7, 128.5, 127.41, 127.36, 79.0, 42.8; HRMS-ESI(−) m/z calcd for $C_{12}H_{11}N_3O_5$ 276.0626 [M-H]−, found 276.0628. The INST $IC_{50}$ for this compound is 37±21 μM.

N-(4-Fluorobenzyl)-7-(hydroxy)-2,3,4,6,7,8-hexahydro-6,8-dioxo-1H-pyrimido[1,6-a]pyrimidine-9-carboxamide (17)

Pale white solid, 96 yield; $^1$H NMR (600 MHz, DMSO-d6): δ 11.52 (s, 1H), 10.29 (s, 1H), 10.02 (br s, 1H), 7.31-7.13 (m, 4H), 4.42 (d, J=4.8, 2H), 3.82 (m, 2H), 3.38 (m, 2H), 1.94 (m, 2H); $^{13}$C NMR (150 MHz, DMSO-d6): δ 167.9, 161.1 (d, $J_{CF}$=241.5 Hz), 160.4, 154.1, 147.4, 136.0 (d, $J_{CF}$=2.3 Hz), 129.1 (d, $J_{CF}$=8.1 Hz), 115.0 (d, $J_{CF}$=20.1 Hz), 78.6, 41.0, 40.8, 38.1, 18.8; HRMS-ESI(−) m/z calcd for $C_{15}H_{15}FN_4O_4$ 333.1005 [M-H]−, found 333.1001. The INST $IC_{50}$ for this compound is 0.43±0.13 μM.

Biology

INST Assay.

HIV integrase was expressed and purified as previously reported.[43] Inhibition assays were performed using a modified protocol of a reported method.[43] Briefly, 2.1 μL of compound suspended in DMSO was placed in duplicate into a Black 96 well non-binding plate (coming 3991). Compounds were plated in duplicate to a final concentration of 0.13-100 μM. To each well of the plate 186.9 μL of reaction mixture without DNA substrate was added (10 mM HEPES pH 7.5, 10% glycerol w/v, 10 mM MnCl2, 1 mM DTT, 1 μM integrase). The enzyme was incubated with inhibitor for 10 min at 25° C. after which the reaction was initiated by the addition of 21 μL of 500 nM oligo (5' biotin ATGTGGAAAATCTCTAGCA annealed with ACTGCTAGAGATTTTCCACAT 3' Cy5). Reactions were incubated at 37° C. for 30 min and then quenched by the addition of 5.2 μL 500 mM EDTA. Each reaction was moved (200 μL) to a MultiScreen HTS PCR plate (Millipore MSSLBPC10) containing 20 μL streptavidin agarose beads (Life Technologies S951) and incubated with shaking for 30 min. A vacuum manifold was used to remove the reaction mixture and the beads were similarly washed 3 times with wash buffer (0.05% SDS, 1 mM EDTA in PBS). The plates were further washed 3 times with 200 μL 50 mM NaOH to denature DNA not covalently linked to the biotin modification. For each denaturation step the plate was incubated with shaking at 25° C. for 5 min and the NaOH was removed by centrifugation at 1000 g for 1 min. The reaction products were eluted from the beads by the addition of 150 μL formamide. The plate was incubated at 25° C. for 10 min and read directly at 635/675 in a SpectraMax i3 plate reader (Molecular Devices). Expression and purification of the recombinant IN in *Escherichia coli* were performed as previously reported[39,44] with addition of 10% glycerol to all buffers. Preparation of oligonucleotide substrates has been described.[45] Integrase reactions were performed in 10 μL with 400 nM of recombinant IN, 20 nM of 5'-end [$^{32}$P]-labeled oligonucleotide substrate and inhibitors at various concentrations. Solutions of 10% DMSO without inhibitors were used as controls. Reactions were incubated at 37° C. (60 minutes) in buffer containing 50 mM MOPS, pH 7.2, 7.5 mM $MgCl_2$, and 14.3 mM 2-mercaptoethanol. Reactions were stopped by addition of 10 μL of loading dye (10 mM EDTA, 98% deionized formamide, 0.025% xylene cyanol and 0.025% bromophenol blue). Reactions were then subjected to electrophoresis in 20% polyacrylamide-7 M urea gels. Gels were dried and reaction products were visualized and quantitated with a Typhoon 8600 (GE Healthcare, Little Chalfont, Buckinghamshire, UK). Densitometric analyses were performed using ImageQuant from Molecular Dynamics Inc. The concentrations at which enzyme activity was reduced by 50% ($IC_{50}$) were determined using "Prism" software (GraphPad Software, San Diego, Calif.) for nonlinear regression to fit dose-response data to logistic curve models.

HIV-1 Antiviral Assay.

The HIV Cytoprotection assay used CEM-SS cells and the IIIB strain of HIV-1. Briefly virus and cells were mixed in the presence of test compound and incubated for 6 days. The virus was pre-titered such that control wells exhibit 70 to 95% loss of cell viability due to virus replication. Therefore, antiviral effect or cytoprotection was observed when compounds prevent virus replication. Each assay plate contained cell control wells (cells only), virus control wells (cells plus virus), compound toxicity control wells (cells plus compound only), compound colorimetric control wells (compound only) as well as experimental wells (compound plus cells plus virus). Cytoprotection and compound cytotoxicity were assessed by MTS (CellTiter® 96 Reagent, Promega, Madison Wis.) and the $EC_{50}$ (concentration inhibiting virus replication by 50%), $CC_{50}$ (concentration resulting in 50% cell death) and a calculated TI (therapeutic index $CC_{50}/EC_{50}$) were provided. Each assay included AZT as a positive control.

Modeling and Docking.

All modeling study was carried out using schrodinger modeling suite[46] based on a homology model[36] of HIV-1 IN CCD-DNA complex using Glide with standard precision protocol.[47] The $Mg^{2+}$ ions and the interfacial hydrophobic pocket between the HIV-1 IN and DNA were defined as required constraints. The van der Waals radii of non-polar atoms for each of the ligands were scaled by a factor of 0.8 to account for structure variability to specific ligand binding.

DOCUMENTS CITED

1. Tang. J., K. Maddali, C. D. Dreis, Y. Y. Sham, R. Vince. Y. Pommier, and Z. Wang, N-3 Hydroxylation of Pyrimidine-2,4-diones Yields Dual Inhibitors of HIV Reverse Transcriptase and Integrase. ACS Med. Chem. Lett. 2011. 2 63-67.
2. Tang, J., K. Maddali. C. D. Dreis, Y. Y. Sham, R. Vince, Y. Pommier, and Z. Q. Wang, 6-Benzoyl-3-hydroxypyrimidine-2,4-diones as dual inhibitors of HIV reverse transcriptase and integrase. Bioorg. Med. Chem. Lett. 2011.21 2400-2402.
3. Tang, J., K. Maddali, M. Metifiot, Y. Y. Sham, R. Vince, Y. Pommier, and Z. Q. Wang, 3-Hydroxypyrimidine-2,4-diones as an Inhibitor Scaffold of HIV Integrase. J. Med. Chem. 2011.54 2282-2292.
4. Mai, X., X. Lu, H. Xia, Y. Cao, Y. Liao, and X. Lv, Synthesis, antitumor evaluation and crystal structure of hydroxyurea derivatives. Chem. Pharm. Bull. 2010. 58 94-7.
5. Stadlbauer. W., E. S. Badawey, G. Hojas, P. Roschger, and T. Kappe, Malonates in cyclocondensation reactions. Molecules 2001. 6 338-352.
6. Arnott, E. A., L. C. Chan, B. G. Cox, B. Meyrick, and A. Phillips. POCl3 Chlorination of 4-Quinazolones. J. Org. Chem. 2011. 76 1653-1661.
7. Kotera, M., K. Ishii. O. Tamura, and M. Sakamoto, 1,3-dipolar cycloadditions of photoinduced carbonyl ylides. Part 2. Photoreactions of alpha,beta-unsaturated gamma,delta-epoxy dinitriles and ethyl vinyl ether. J. Chem. Soc.-Perkin Transactions 1 1998 313-318.
8. Lee, I. Y., J. Y. Lee, and Y. D. Gong, Microwave-assisted facile one-step carbamoylation of 6-aminouracils. Synthesis 2005 2713-2717.
9. Fletcher, S, and P. T. Gunning, Mild, efficient and rapid O-debenzylation of ortho-substituted phenols with trifluoroacetic acid. Tetrahedron Lett. 2008. 49 4817-4819.
10. Bagasra, O., A unified concept of HIV latency. Expert Opin. Biol. Ther. 2006. 61135-1149.
11. Chun, T.-W., L. Stuyver, S. B. Mizell, L. A. Ehler, J. A. M. Mican, M. Baseler, A. L. Lloyd, M. A. Nowak, and A. S. Fauci, Presence of an inducible HIV-1 latent reservoir during highly active antiretroviral therapy. Proc. Natl. Acad. Sci. USA 1997. 94 13193-13197.
12. Finzi, D., M. Hermankova, T. Pierson, L. M. Carruth, C. Buck, R. E. Chaisson, T. C. Quinn. K. Chadwick, J. Margolick. R. Brookmeyer, J. Gallant, M. Markowitz, D. D. Ho, D. D. Richman, and R. F. Siliciano, Identification of a reservoir for HIV-1 in patients on highly active antiretroviral therapy. Science 1997. 278 1295-1300.
13. Pommier. Y., A. A. Johnson, and C. Marchand, Integrase inhibitors to treat HIV/AIDS. Nat. Rev. Drug Discovery 2005.4 236-248.
14. Cotelle, P., Patented HIV-1 integrase inhibitors (1998-2005). Recent Pat. Anti-Infect. Drug Discovery 2006. 1 1-15.
15. Henao-Mejia, J., Y. Goez, P. Patino, and M. T. Rugeles, Diketo acids derivatives as integrase inhibitors: the war against the acquired immunodeficiency syndrome. Recent Pat. Anti-Infect. Drug Discovery 2006. 1 255-265.
16. Dubey. S., Y. D. Satyanarayana, and H. Lavania, Development of integrase inhibitors for treatment of AIDS: An overview. Eur. J. Med Chem. 2007. 42 1159-1168.
17. Marchand, C., K. Maddali, M. Metifiot, and Y. Pommier, HIV-1 IN inhibitors: 2010 update and perspectives. Curr. Top. Med. Chem. 2009. 9 1016-1037.
18. Dayam, R., T. Sanchez, and N. Neamati, Diketo Acid Pharmacophore. 2. Discovery of Structurally Diverse Inhibitors of HIV-1 Integrase. J. Med. Chem. 2005. 48 8009.
19. Dayam, R., T. Sanchez, O. Clement, R. Shoemaker, S. Sei, and N. Neamati, b-Diketo acid pharmacophore hypothesis. 1. Discovery of a novel class of HIV-1 integrase inhibitors. J. Med. Chem. 2005. 48 111.
20. Deng, J., T. Sanchez, N. Neamati, and J. M. Briggs, Dynamic Pharmacophore Model Optimization: Identification of Novel HIV-1 Integrase Inhibitors. J. Med. Chem. 2006. 49 1684-1692.
21. Barreca, M. L., S. Ferm, A. Rao. L. De Luca, M. Zappala, A.-M. Monforte, Z. Debyser, M. Witvrouw, and A. Chimirri, Pharmacophore-Based Design of HIV-1 Integrase Strand-Transfer Inhibitors. J. Med. Chem. 2005. 48 7084-7088.

22. Mustata, G. I., A. Brigo, and J. M. Briggs, HIV-1 integrase pharmacophore model derived from diverse classes of inhibitors. *Bioorg. Med. Chem. Lett.* 2004. 14 1447-1454.
23. Carlson, H. A., K. M. Masukawa, K. Rubins, F. D. Bushman, W. L. Jorgensen, R. D. Lins, J. M. Briggs, and J. A. McCammon, Developing a Dynamic Pharmacophore Model for HIV-1 Integrase. *J. Med. Chem.* 2000. 43 2100-2114.
24. Cocohoba, J, and B. J. Dong, Raltegravir: the first HIV integrase inhibitor. *Clin. Ther.* 2008. 30 1747-1765.
25. Summa. V., A. Petrocchi, F. Bonelli, B. Crescenzi, M. Donghi. M. Ferrara, F. Fiore, C. Gardelli, O. Gonzalez Paz, D. J. Hazuda, P. Jones, O. Kinzel, R. Laufer, E. Monteagudo, E. Muraglia, E. Nizi, F. Orvieto, P. Pace, G. Pescatore, R. Scarpelli, K. Stillmock, M. V. Witmer, and M. Rowley, Discovery of Raltegravir, a Potent. Selective Orally Bioavailable HIV-Integrase Inhibitor for the Treatment of HIV-AIDS Infection. *J. Med. Chem.* 2008. 51 5843-5855.
26. Shimura. K, and E. N. Kodama, Elvitegravir: a new HIV integrase inhibitor. *Antiviral Chem. Chemother.* 2009. 20 79-85.
27. Vandekerckhove, L., GSK-1349572, a novel integrase inhibitor for the treatment of HIV infection. *Curr. Opin. Invest. Drugs* 2010. 11 203-212.
28. Min, S., I. Song, J. Borland, S. Chen, Y. Lou, T. Fujiwara, and S. C. Piscitelli, Pharmacokinetics and safety of S/GSK1349572, a next-generation HIV integrase inhibitor, in healthy volunteers. *Antimicrob. Agents Chemother.* 2009. 54 254-258.
29. Prada, N, and M. Markowitz, Novel integrase inhibitors for HIV. *Expert Opin Investig Drugs* 2010. 19 1087-98.
30. Esposito, D, and R. Craigie, HIV integrase structure and function. *Advances in Virus Research* 1999. 52 319-333.
31. Goldgur, Y., F. Dyda, A. B. Hickman, T. M. Jenkins, R. Craigie, and D. R. Davies, Three new structures of the core domain of HIV-1 integrase: an active site that binds magnesium. *Proc. Natl. Acad. Sci. USA.* 1998. 95 9150-9154.
32. Dyda, F., A. B. Hickman, T. M. Jenkins, A. Engelman, R. Craigie, and D. R. Davies, Crystal structure of the catalytic domain of HIV-1 integrase: similarity to other polynucleotidyl transferases. *Science* 1994. 266 1981-6.
33. O'Brien, C., HIV Integrase Structure Catalyzes Drug Search. *Science* 1994. 266 1946.
34. Hare, S., S. S. Gupta, E. Valkov, A. Engelman, and P. Cherepanov, Retroviral intasome assembly and inhibition of DNA strand transfer. *Nature* 2010. 464 232-236.
35. Hare, S., A. M. Vosb, R. F. Claytonb, J. W. Thuringb, M. D. Cummingsb, and P. Cherepanov, Molecular mechanisms of retroviral integrase inhibition and the evolution of viral resistance. *Proc. Natl. Acad. Sci.* USA 2010 10.1073/pnas.1010246107.
36. Tang, J., K. Maddali, Y. Pommier, Y. Y. Sham, and Z. Wang, Scaffold rearrangement of dihydroxypyrimidine inhibitors of HIV integrase: Docking model revisited. *Bioorg. Med. Chem. Lett.* 2010. 20 3275-3279.
37. Krishnan, L., X. Li, H. L. Naraharisetty, S. Hare, P. Cherepanov, and A. Engelman, Structure-based modeling of the functional HIV-1 intasome and its inhibition. *Proc. Natl. Acad. Sci. U.S.A.* 2010. 2010 1-6, 6 pp.
38. Metifiot, M., C. Marchand, K. Maddali, and Y. Pommier, Resistance to integrase inhibitors. *Viruses* 2010. 2 1347-1366.
39. Metifiot, M., K. Maddali, A. Naumova, X. Zhang. C. Marchand, and Y. Pommier, Biochemical and Pharmacological Analyses of HIV-1 Integrase Flexible Loop Mutants Resistant to Raltegravir. Biochemistry 2010. 49 3715-3722.
40. da Silva, D., L. Van Wesenbeeck, D. Breilh, S. Reigadas. G. Anies. K. Van Baelen, P. Morlat, D. Neau, M. Dupon, L. Wittkop, H. Fleury, and B. Masquelier, HIV-1 resistance patterns to integrase inhibitors in antiretroviral-experienced patients with virological failure on raltegravir-containing regimens. *J. Antimicrob. Chemother.* 2010. 65 1262-1269.
41. Reuman. E. C., M. H. Bachmann. V. Varghese, W. J. Fessel, and R. W. Shafer, Panel of Prototypical Raltegravir-Resistant Infectious Molecular Clones in a Novel Integrase-Deleted Cloning Vector. *Antimicrobial Agents and Chemotherapy* 2010. 54 934-936.
42. Fantauzzi, A, and I. Mezzaroma, Dolutegravir: clinical efficacy and role in HIV therapy. *Ther Adv Chronic Dis* 2014. 5 164-77.
43. Wang, Z., E. M. Bennett, D. J. Wilson, C. Salomon, and R. Vince, Rationally designed dual inhibitors of HIV reverse transcriptase and integrase. *J. Med. Chem.* 2007. 50 3416-3419.
44. Leh, H., P. Brodin, J. Bischerour, E. Deprez, P. Tauc, J. C. Brochon, E. LeCam, D. Coulaud, C. Auclair, and J. F. Mouscadet. Determinants of Mg2+-dependent activities of recombinant human immunodeficiency virus type 1 integrase. *Biochemistry* 2000. 39 9285-9294.
45. Semenova, E. A., A. A. Johnson, C. Marchand, D. A. Davis, R. Yarchoan, and Y. Pommier, Preferential inhibition of the magnesium-dependent strand transfer reaction of HIV-1 integrase by α-hydroxytropolones. *Mol. Pharmacol.* 2006. 69 1454-1460.
46. Maestro v9.1, G.v., Macromodel v9.8, Liason v5.6. Schrodinger, LLC: New York.
47. Friesner, R. A., J. L. Banks, R. B. Murphy, T. A. Halgren, J. J. Klicic, D. T. Mainz, M. P. Repasky, E. H. Knoll, M. Shelley, J. K. Perry, D. E. Shaw, P. Francis, and P. S. Shenkin, Glide: a new approach for rapid, accurate docking and scoring. 1. Method and assessment of docking accuracy. *J. Med. Chem.* 2004. 47 1139-1149.

While the invention has been described and exemplified in sufficient detail for those skilled in this art to make and use it, various alternatives, modifications, and improvements will be apparent to those skilled in the art without departing from the spirit and scope of the claims.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Provided herein are the following embodiments, the numbering of which is not to be construed as designating levels of importance:

Embodiment 1 relates to a compound of formula (I)

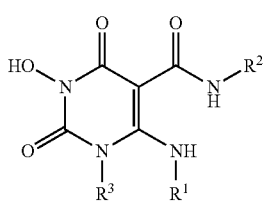

(I)

wherein $R^1$ is H, $(C_1$-$C_6)$alkyl, $(C_3$-$C_6)$ cycloalkyl, or $(C_6$-$C_{12})$aryl; $R^2$ is benzyl, which can be unsubstituted or can be substituted with one to three occurrences of a substituent independently selected from the group consisting of fluoro, chloro, bromo, iodo, cyano, nitro, $(C_1$-$C_6)$alkyl, $(C_1$-$C_6)$alkoxy, $(C_1$-$C_6)$alkoxycarbonyl, $(C_1$-$C_6)$alkylC(=O)NH, $(C_1$-$C_6)$alkylNHC(=O), $((C_1$-$C_6)$alkyl$)_2$NC(=O), $(C_1$-$C_6)$alkylSO$_2$, $(C_1$-$C_6)$alkylNHSO$_2$, and $((C_1$-$C_6)$alkyl$)_2$NSO$_2$; $R^3$ is H, $(C_1$-$C_6)$alkyl, $(C_3$-$C_6)$ cycloalkyl, or $(C_6$-$C_{12})$aryl; or a pharmaceutically acceptable salt thereof; or a compound of formula (II)

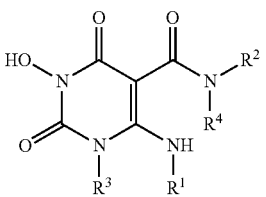

(II)

wherein $R^1$ is H, $(C_1$-$C_6)$alkyl, $(C_3$-$C_6)$ cycloalkyl, or $(C_6$-$C_{12})$aryl; $R^2$ is hydrogen, benzyl, which can be unsubstituted or can be substituted with one to three occurrences of a substituent independently selected from the group consisting of fluoro, chloro, bromo, iodo, cyano, nitro, $(C_1$-$C_6)$alkyl, $(C_1$-$C_6)$alkoxy, $(C_1$-$C_6)$alkoxycarbonyl, $(C_1$-$C_6)$alkylC(=O)NH, $(C_1$-$C_6)$alkylNHC(=O), $((C_1$-$C_6)$alkyl$)_2$NC(=O), $(C_1$-$C_6)$alkylSO$_2$, $(C_1$-$C_6)$alkylNHSO$_2$, and $((C_1$-$C_6)$alkyl$)_2$NSO$_2$; $R^3$ is H, $(C_1$-$C_6)$alkyl, $(C_3$-$C_6)$ cycloalkyl, or $(C_6$-$C_{12})$aryl or $R^1$ and $R^3$ can form a five- or six-membered heterocyclic ring; and $R^4$ is a hydrogen or $(C_1$-$C_6)$alkyl; or a pharmaceutically acceptable salt thereof. In some embodiments, $R^1$ and $R^3$ can form a five- or six-membered heterocyclic ring; or a compound of formula (III)

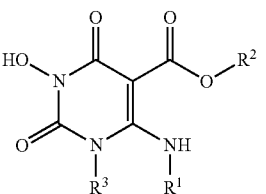

(III)

wherein $R^1$ is H, $(C_1$-$C_6)$alkyl, $(C_3$-$C_6)$ cycloalkyl, or $(C_6$-$C_{12})$aryl; $R^2$ is $(C_3$-$C_6)$ cycloalkyl, or $(C_6$-$C_{12})$aryl; and $R^3$ is H, $(C_1$-$C_6)$alkyl, $(C_3$-$C_6)$ cycloalkyl, or $(C_6$-$C_{12})$aryl or $R^1$ and $R^2$ can form a five- or six-membered heterocyclic ring;

or a pharmaceutically acceptable salt thereof. In some embodiments, $R^1$ and $R^3$ can form a five- or six-membered heterocyclic ring; or a compound of formula (IV)

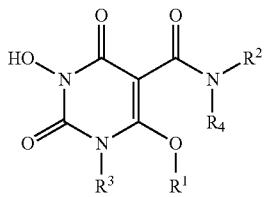

(IV)

wherein $R^1$ is H, $(C_1$-$C_6)$alkyl, $(C_3$-$C_6)$ cycloalkyl, or $(C_6$-$C_{12})$aryl; $R^2$ is $(C_3$-$C_6)$ cycloalkyl, or $(C_6$-$C_{12})$aryl; $R^3$ is H, $(C_1$-$C_6)$alkyl, $(C_3$-$C_6)$ cycloalkyl, or $(C_6$-$C_{12})$aryl or $R^1$ and $R^3$ can form a five- or six-membered heterocyclic ring; and $R^4$ is a hydrogen or $(C_1$-$C_6)$alkyl; or a pharmaceutically acceptable salt thereof.

Embodiment 2 relates to a compound of Embodiment 1, wherein the compound is of formula (IA)

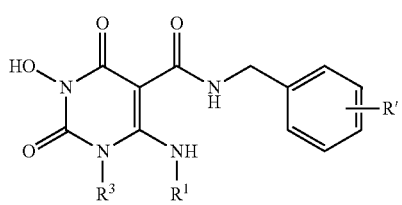

(IA)

wherein $R^1$ is H, $(C_1$-$C_6)$alkyl or $(C_3$-$C_6)$ cycloalkyl, and R' is zero to three occurrences of a substituent independently selected from the group consisting of fluoro, chloro, bromo, iodo, cyano, nitro, $(C_1$-$C_6)$alkyl, $(C_1$-$C_6)$alkoxy, $(C_1$-$C_6)$alkoxycarbonyl, $(C_1$-$C_6)$alkylC(=O)NH, $(C_1$-$C_6)$alkylNHC(=O), $((C_1$-$C_6)$alkyl$)_2$NC(=O), $(C_1$-$C_6)$alkylSO$_2$, $(C_1$-$C_6)$alkylNHSO$_2$, and $((C_1$-$C_6)$alkyl$)_2$NSO$_2$; $R^3$ is H, $(C_1$-$C_6)$ alkyl, $(C_3$-$C_6)$ cycloalkyl, or $(C_6$-$C_{12})$aryl; or a pharmaceutically acceptable salt thereof.

Embodiment 3 relates to a compound of Embodiments 1-2, wherein $R^1$ is hydrogen, methyl or ethyl; or wherein $R^3$ is hydrogen; or both.

Embodiment 4 relates to a compound of Embodiments 1-3, wherein R' is a one or two occurrences of fluoro, or one occurrence of fluoro and one occurrence of chloro.

Embodiment 5 relates to a compound of Embodiments 1-4, wherein the compound is any one of:

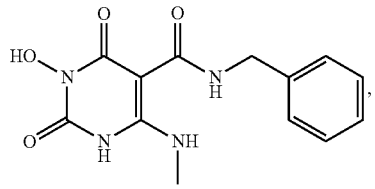

,

-continued

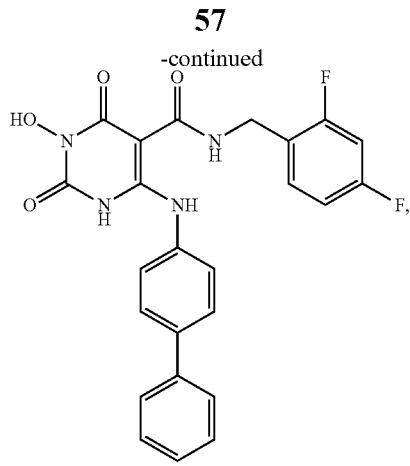
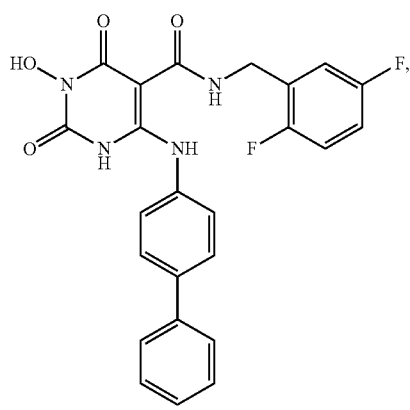
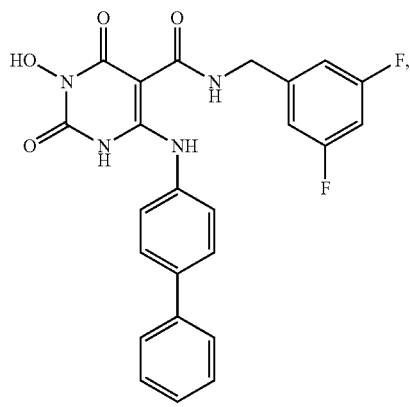
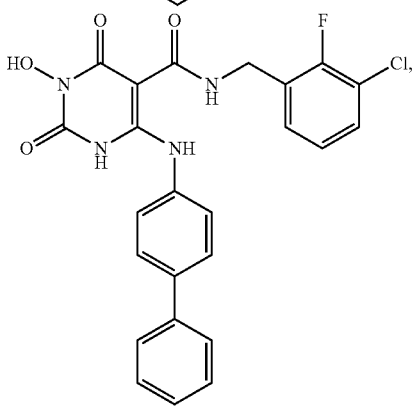

or a pharmaceutically acceptable salt thereof.

Embodiment 6 relates to a compound of Embodiments 1-5, wherein the compound has a half maximal HIV-1 integrase strand transfer inhibitory concentration ($IC_{50}$) of from about 1 nM to about 250 µM.

Embodiment 7 relates to a compound of Embodiments 1-6, wherein the compound has a half maximal effective concentration ($EC_{50}$) of from about 1 nM to about 250 nM.

Embodiment 8 relates to a compound of Embodiments 1-7, wherein the compound has a half maximal cytotoxic concentration ($CC_{50}$) of from about 10 µM to about 100 µM and a therapeutic index of from about 70 to about 2000.

Embodiment 9 relates to a method of inhibiting the human immunodeficiency virus (HIV) integrase, comprising contacting the HIV integrase with an effective amount or concentration of a compound of Embodiments 1-8.

Embodiment 10 relates to the method of Embodiment 9, wherein the contacting is in an intact virus in vivo in a human host.

Embodiment 11 relates to a method of treating a patient afflicted with Acquired Immunodeficiency Syndrome (AIDS), comprising administering to the patient an effective dose of a compound of Embodiments 1-8.

Embodiment 12 relates to the method of Embodiment 11, further comprising administering to the patient an effective dose of a second antiviral compound.

Embodiment 13 relates to the method of Embodiment 12, wherein the second antiviral compound is a protease inhibitor or a reverse transcriptase inhibitor.

Embodiment 14 relates to a pharmaceutical composition comprising a compound of Embodiments 1-8 and a pharmaceutically acceptable excipient.

Embodiment 15 relates compound of Embodiments 1-8 for treatment of Acquired Immunodeficiency Syndrome (AIDS) in a human patient afflicted therewith.

Embodiment 16 relates to the use of a compound of Embodiments 1-8 for preparation of a medicament effective for the treatment of Acquired Immunodeficiency Syndrome (AIDS) in a human patient afflicted therewith.

What is claimed is:

1. A compound of formula (I)

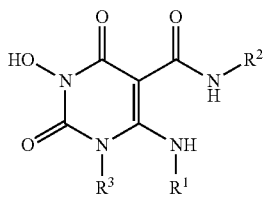

(I)

wherein $R^1$ is H, $(C_1-C_6)$alkyl, $(C_3-C_6)$ cycloalkyl, or $(C_6-C_{12})$aryl; $R^2$ is benzyl, which can be unsubstituted or can be substituted with one to three occurrences of a substituent independently selected from the group consisting of fluoro, chloro, bromo, iodo, cyano, nitro, $(C_1-C_6)$alkyl, $(C_1-C_6)$alkoxy, $(C_1-C_6)$alkoxycarbonyl, $(C_1-C_6)$alkylC(=O)NH, $(C_1-C_6)$alkylNHC(=O), $((C_1-C_6)$alkyl$)_2$NC(=O), $(C_1-C_6)$alkylSO$_2$, $(C_1-C_6)$alkylNHSO$_2$, and $((C_1-C_6)$alkyl$)_2$NSO$_2$; $R^3$ is H, $(C_1-C_6)$alkyl, $(C_3-C_6)$ cycloalkyl, or $(C_6-C_{12})$aryl; or a pharmaceutically acceptable salt thereof; or a compound of formula (II)

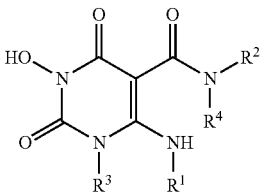

(II)

wherein $R^1$ is H, $(C_1-C_6)$alkyl, $(C_3-C_6)$ cycloalkyl, or $(C_6-C_{12})$aryl; $R^2$ is hydrogen, benzyl, which can be unsubstituted or can be substituted with one to three occurrences of a substituent independently selected from the group consisting of fluoro, chloro, bromo, iodo, cyano, nitro, $(C_1-C_6)$alkyl, $(C_1-C_6)$alkoxy, $(C_1-C_6)$alkoxycarbonyl, $(C_1-C_6)$alkylC(=O)NH, $(C_1-C_6)$alkylNHC(=O), $((C_1-C_6)$alkyl$)_2$NC(=O), $(C_1-C_6)$alkylSO$_2$, $(C_1-C_6)$alkylNHSO$_2$, and $((C_1-C_6)$alkyl$)_2$NSO$_2$; $R^3$ is H, $(C_1-C_6)$alkyl, $(C_3-C_6)$ cycloalkyl, or $(C_6-C_{12})$aryl or $R^1$ and $R^3$ can form a five- or six-membered heterocyclic ring; and $R^4$ is a hydrogen or $(C_1-C_6)$alkyl; or a pharmaceutically acceptable salt thereof, In some embodiments, $R^1$ and $R^3$ can form a five- or six-membered heterocyclic ring; or a compound of formula (III)

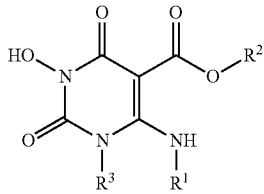

(III)

wherein $R^1$ is H, $(C_1-C_6)$alkyl, $(C_3-C_6)$ cycloalkyl, or $(C_6-C_{12})$aryl; $R^2$ is $(C_3-C_6)$ cycloalkyl, or $(C_6-C_{12})$aryl; and $R^3$ is H, $(C_1-C_6)$alkyl, $(C_3-C_6)$ cycloalkyl, or $(C_6-C_{12})$aryl or $R^1$ and $R^3$ can form a five- or six-membered heterocyclic ring; or a pharmaceutically acceptable salt thereof, In some embodiments, $R^1$ and $R^3$ can form a five- or six-membered heterocyclic ring; or a compound of formula (IV)

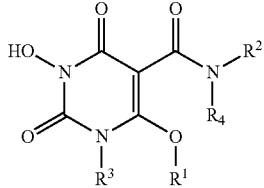

(IV)

wherein $R^1$ is H, $(C_1-C_6)$alkyl, $(C_3-C_6)$ cycloalkyl, or $(C_6-C_{12})$aryl; $R^2$ is $(C_3-C_6)$ cycloalkyl, or $(C_6-C_{12})$aryl; $R^3$ is H, $(C_1-C_6)$alkyl, $(C_3-C_6)$ cycloalkyl, or $(C_6-C_{12})$aryl or $R^1$ and $R^3$ can form a five- or six-membered heterocyclic ring; and $R^4$ is a hydrogen or $(C_1-C_6)$alkyl; or a pharmaceutically acceptable salt thereof.

2. The compound of claim 1, wherein the compound is of formula (IA)

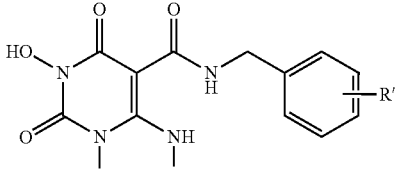

(IA)

wherein $R^1$ is H, $(C_1-C_6)$alkyl or $(C_3-C_6)$ cycloalkyl, and R' is zero to three occurrences of a substituent independently selected from the group consisting of fluoro, chloro, bromo, iodo, cyano, nitro, $(C_1-C_6)$alkyl, $(C_1-C_6)$alkoxy, $(C_1-C_6)$alkoxycarbonyl, $(C_1-C_6)$alkylC(=O)NH, $(C_1-C_6)$alkylNHC(=O), $((C_1-C_6)$alkyl$)_2$NC(=O), $(C_1-C_6)$alkylSO$_2$, $(C_1-C_6)$alkylNHSO$_2$, and $((C_1-C_6)$alkyl$)_2$NSO$_2$; $R^3$ is H, $(C_1-C_6)$alkyl, $(C_3-C_6)$ cycloalkyl, or $(C_6-C_{12})$aryl; or a pharmaceutically acceptable salt thereof.

3. The compound of claim 2, wherein $R^1$ is hydrogen, methyl or ethyl; or wherein $R^3$ is hydrogen; or both.

4. The compound of claim 3, wherein R' is a one or two occurrences of fluoro, or one occurrence of fluoro and one occurrence of chloro.
5. The compound of claim 1, wherein the compound is any one of:
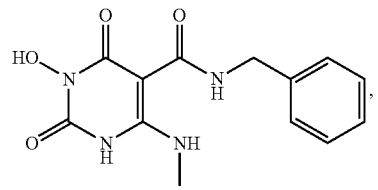
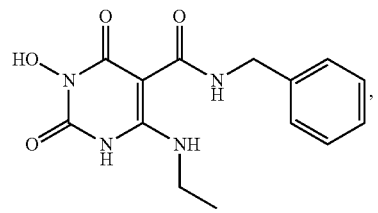
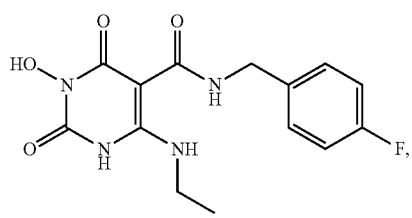
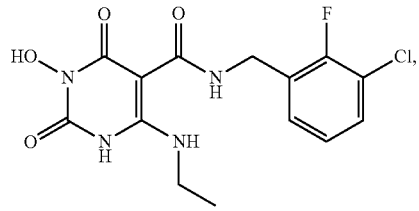
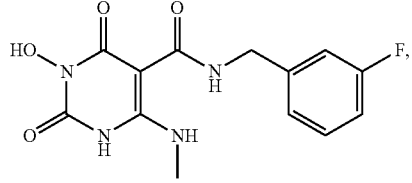
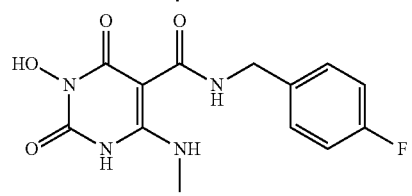
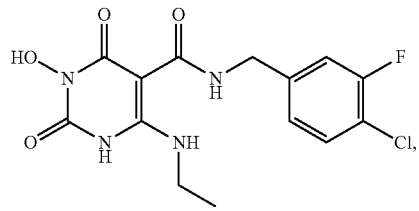
-continued
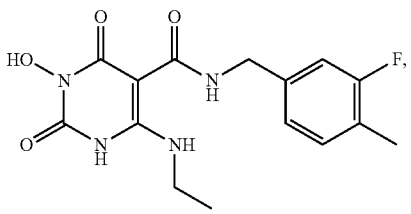
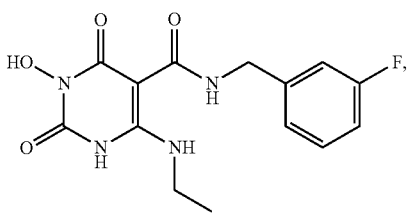
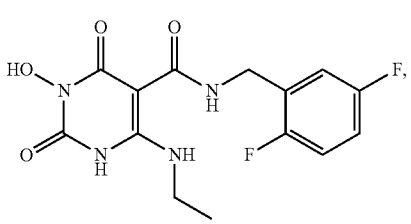
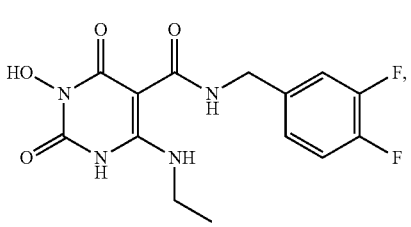
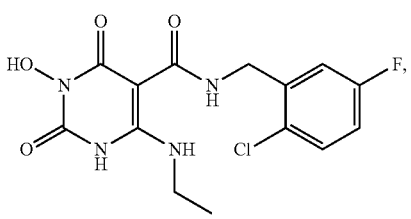
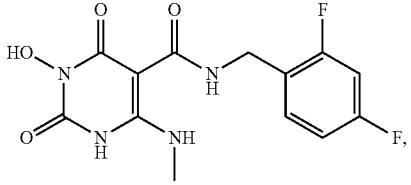
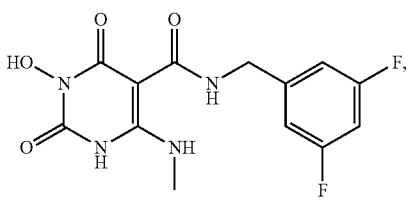

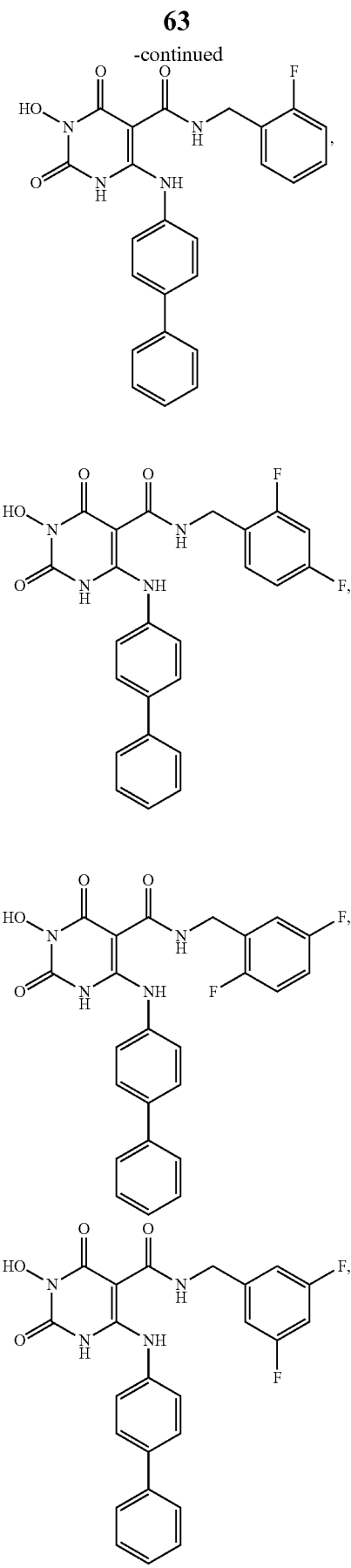
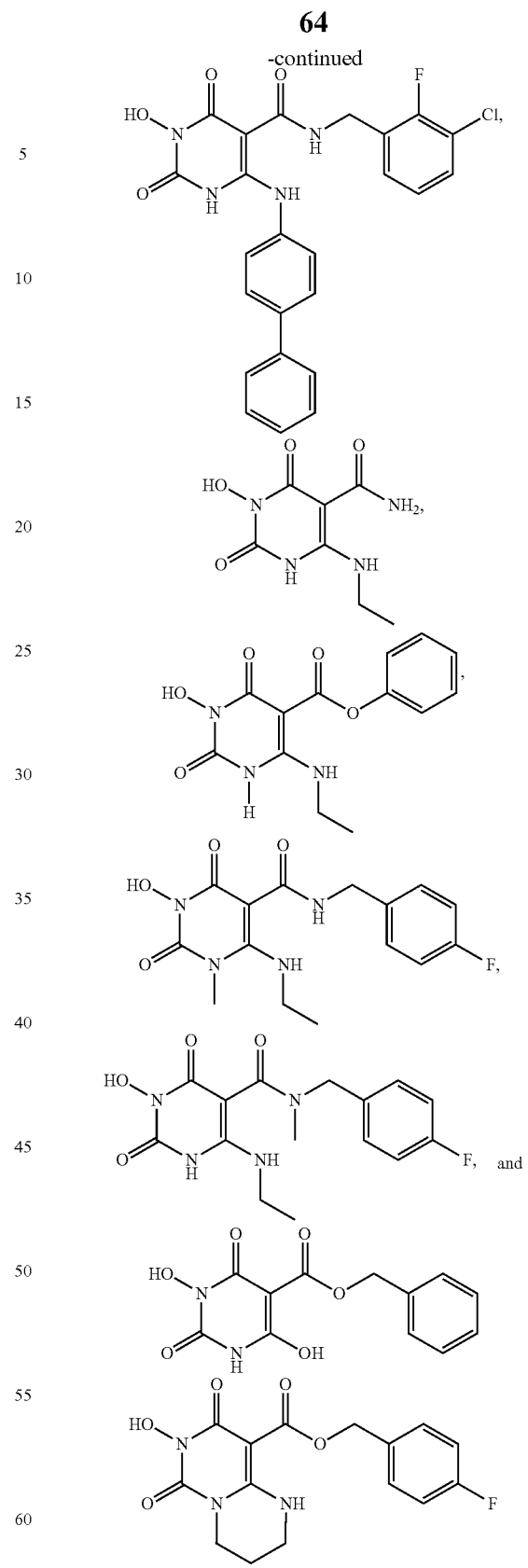
or a pharmaceutically acceptable salt thereof.
6. The compound of claim 1, wherein the compound has a half maximal HIV-1 integrase strand transfer inhibitory concentration ($IC_{50}$) of from about 1 nM to about 250 μM.

7. The compound of claim 1, wherein the compound has a half maximal effective concentration ($EC_{50}$) of from about 1 nM to about 250 nM.

8. The compound of claim 1, wherein the compound has a half maximal cytotoxic concentration ($CC_{50}$) of from about 10 µM to about 100 µM and a therapeutic index of from about 70 to about 2000.

9. A method of inhibiting the human immunodeficiency virus (HIV) integrase, comprising contacting the HIV integrase with an effective amount or concentration of a compound of claim 1.

10. The method of claim 9, wherein the contacting is in an intact virus in vivo in a human host.

11. A method of treating a patient afflicted with Acquired Immunodeficiency Syndrome (AIDS), comprising administering to the patient an effective dose of a compound of claim 1.

12. The method of claim 11, further comprising administering to the patient an effective dose of a second antiviral compound.

13. The method of claim 12, wherein the second antiviral compound is a protease inhibitor or a reverse transcriptase inhibitor.

14. A pharmaceutical composition comprising a compound of claim 1 and a pharmaceutically acceptable excipient.

* * * * *